United States Patent
Vicario et al.

(10) Patent No.: US 11,224,379 B2
(45) Date of Patent: Jan. 18, 2022

(54) ENHANCEMENT OF RESPIRATORY PARAMETER ESTIMATION AND ASYNCHRONY DETECTION ALGORITHMS VIA THE USE OF CENTRAL VENOUS PRESSURE MANOMETRY

(71) Applicant: KONINKLIJKE PHILIPS N.V., Eindhoven (NL)

(72) Inventors: Francesco Vicario, Boston, MA (US); Nikolaos Karamolegkos, New York, NY (US); Antonio Albanese, Mission Viejo, CA (US); Nicolas Wadih Chbat, White Plains, NY (US)

(73) Assignee: Koninklljke Philips N.V., Eindhoven (NL)

( * ) Notice: Subject to any disclaimer, the term of this patent is extended or adjusted under 35 U.S.C. 154(b) by 658 days.

(21) Appl. No.: 15/999,588

(22) PCT Filed: Feb. 1, 2017

(86) PCT No.: PCT/EP2017/052140
§ 371 (c)(1),
(2) Date: Aug. 17, 2018

(87) PCT Pub. No.: WO2017/140500
PCT Pub. Date: Aug. 24, 2017

(65) Prior Publication Data
US 2021/0205558 A1 Jul. 8, 2021

Related U.S. Application Data

(60) Provisional application No. 62/296,666, filed on Feb. 18, 2016.

(51) Int. Cl.
*A61M 16/00* (2006.01)
*A61B 5/00* (2006.01)

(52) U.S. Cl.
CPC ....... *A61B 5/4836* (2013.01); *A61M 16/0057* (2013.01); *A61M 16/024* (2017.08);
(Continued)

(58) Field of Classification Search
CPC ............ A61M 16/024; A61M 16/0057; A61M 2230/40; A61M 2230/04; A61M 2230/30;
(Continued)

(56) References Cited

U.S. PATENT DOCUMENTS

2003/0225339 A1  12/2003  Orr et al.
2008/0066753 A1  3/2008  Martin et al.
(Continued)

FOREIGN PATENT DOCUMENTS

JP  2012503527 A  9/2009
WO  2014207623 A2  12/2014
(Continued)

OTHER PUBLICATIONS

Albanese et al:"An Integreated Mathematical Model of the Human Cardiopulmonary System: Model Development"; Am J. Physiol Circ Physiol 310:H899-H921, First Published Dec. 18, 2015.
(Continued)

*Primary Examiner* — Margaret M Luarca
(74) *Attorney, Agent, or Firm* — Daniel H. Brean

(57) ABSTRACT

A respiratory monitoring apparatus (10) includes a central venous pressure sensor (24) configured to measure a central venous pressure (CVP) signal of a patient. At least one processor (32, 34, 36, 38, 40, 42, 44, 58) is programmed to process the CVP signal to generate respiratory information for the patient by operations including: segmenting the CVP signal based on detected breath intervals; calculating a surrogate muscle pressure signal from the segmented CVP signal; and filtering the surrogate muscle pressure signal to remove a cardiac activity component a cardiac activity
(Continued)

component of the surrogate respiratory muscle pressure signal.

19 Claims, 15 Drawing Sheets

(52) U.S. Cl.
CPC ..... *A61M 2205/50* (2013.01); *A61M 2230/04* (2013.01); *A61M 2230/30* (2013.01); *A61M 2230/40* (2013.01)

(58) Field of Classification Search
CPC .. A61M 2205/50; A61B 5/0205; A61B 5/021; A61B 5/0215; A61B 5/085
See application file for complete search history.

(56) References Cited

U.S. PATENT DOCUMENTS

| 2010/0145201 A1 | 6/2010 | Westbrook et al. |
| 2010/0317932 A1 | 12/2010 | Ukawa |
| 2014/0116442 A1 | 5/2014 | Martin et al. |
| 2017/0049391 A1 | 2/2017 | Melker |

FOREIGN PATENT DOCUMENTS

| WO | 2015104669 A1 | 7/2015 |
| WO | 2016128846 A1 | 8/2016 |
| WO | 2017055959 A1 | 4/2017 |

OTHER PUBLICATIONS

Vicario et al: "Simultaneous Parameter and Input Estimation of a Respiratory Mechanics Model";6th International Conference on High Performance Scientific Computing, Mar. 2015, pp. 1-10.

ENHANCEMENT OF RESPIRATORY PARAMETER ESTIMATION AND ASYNCHRONY DETECTION ALGORITHMS VIA THE USE OF CENTRAL VENOUS PRESSURE MANOMETRY

CROSS-REFERENCE TO PRIOR APPLICATIONS

This application is the U.S. National Phase application under 35 U.S.C. § 371 of International Application No. PCT/EP2017/052140, filed on Feb. 1, 2017, which claims the benefit of U.S. Provisional Patent Application No. 62/296,666, filed on Feb. 18, 2018. These applications are hereby incorporated by reference herein.

FIELD

The following relates to the medical therapy arts, respiratory therapy arts, medical ventilation arts, and related arts.

BACKGROUND

Respiratory monitoring is performed for diagnosing respiratory ailments and in support of respiratory therapies such as mechanical ventilation. Characterization of the respiratory effort exerted by the patient is of particular importance for optimizing ventilator settings for various support modes, such as pressure support ventilation (PSV). The goal is to provide just sufficient support to maintain effective respiration without over-supporting the patient which can lead to atrophy effects, lung injury, increased difficulty in eventually weaning the patient off the ventilator, under-supporting the patient which can lead to excessive muscle fatigue, or other deleterious effects.

Respiratory effort may be variously quantified. The basic parameter is usually referred to as respiratory muscle pressure $P_{mus}(t)$, that is, the pressure exerted on the lungs by the patient's diaphragm and chest musculature. Work of Breathing (WoB) may be computed from the volume integral of $P_{mus}(t)$ (i.e., $WOB = \int P_{mus}(t)dV$), or the time integral of the product of $P_{mus}(t)$ and flow (i.e., $WOB = \int P_{mus}(t)\dot{V}(t)dt$) over a single breath, while Power of Breathing (PoB) may be computed from the volume integral of $P_{mus}(t)$, or the time integral of the product of $P_{mus}(t)$ and flow over a unit time (e.g., per minute, thus encompassing several breaths). Thus, characterizing the respiratory muscle pressure, $P_{mus}(t)$, is a key step in monitoring respiratory effort.

Known approaches for assessing respiratory muscle pressure include invasive and non-invasive techniques. For example, a non-invasive technique, called the End-Inspiratory Pause maneuver, is used to assess respiratory system resistance and elastance by blocking the airway at the end of the inspiratory phase. $P_{mus}(t)$ can then be calculated via the use of the Equation of Motion of the Lungs, and the measured airway pressure and air flow. This approach relies on certain assumptions that may not be valid in all circumstances, and also is clinically problematic as it interrupts (albeit briefly) life-sustaining respiration. In another example, an invasive technique involves the placement of a balloon-tipped catheter into a patient's esophagus. Esophageal pressure has been shown to be a close proxy of intrapleural pressure and it is used to compute the patient's $P_{mus}$. Other approaches rely upon fitting airway pressure and air flow to an Equation of Motion of the Lungs relating these values and parameterized by respiratory system parameters such as respiratory system resistance, $R_{rs}$ and respiratory system compliance $C_{rs}$ or elastance $E_{rs}$. These approaches also generally rely upon some simplifying assumptions on the patient's true $P_{mus}(t)$ profile in order to evaluate the otherwise undetermined set of equations. These simplifying assumptions may again not be valid under all circumstances. Problems particularly arise during patient-ventilator asynchrony episodes in which the patient's respiratory effort is not well-synchronized with the positive airway pressure applied by the mechanical ventilator.

The following provides new and improved apparatuses and methods which overcome the foregoing problems and others.

BRIEF SUMMARY

In accordance with one aspect, a respiratory monitoring apparatus includes a central venous pressure sensor configured to measure a central venous pressure (CVP) signal of a patient. At least one processor is programmed to process the CVP signal to generate respiratory information for the patient by operations including: segmenting the CVP signal to define breath intervals; calculating a surrogate respiratory muscle pressure signal from the segmented CVP signal; and filtering the surrogate respiratory muscle pressure signal to remove a cardiac activity component of the surrogate respiratory muscle pressure signal.

In accordance with another aspect, a mechanical ventilation apparatus includes a mechanical ventilator. A central venous pressure sensor is configured to measure a central venous pressure signal of a patient as a function of time. At least one airway sensor is configured to measure airway pressure and air flow as a function of time for the patient on the mechanical ventilator. At least one processor is programmed to: receive the central venous pressure signal from the central venous pressure sensor; receive the airway air flow signal as a function of time for the patient from the at least one airway sensor; calculate a surrogate respiratory muscle pressure signal as a function of time for each breath of the patient; extract at least one respiratory characteristic from the surrogate muscle pressure signal by operations including filtering data indicative of cardiac activity of the patient from the respiratory muscle pressure signal, determining a shape of the surrogate muscle pressure signal and updating settings of a constrained optimization algorithm and/or a parametric optimization algorithm of the mechanical ventilator based on the shape-detected signal.

In accordance with another aspect, a non-transitory storage medium stores instructions readable and executable by one or more microprocessors programmed to perform a method of monitoring breathing patterns of a patient. The method includes: receiving a central venous pressure value from a central venous pressure sensor; receiving values of at least one of airway pressure and airway air flow as a function of time for the patient from at least one airway sensor; segmenting the received values to determine each breath of the patient; calculate a surrogate respiratory muscle pressure signal as a function of time for each breath of the patient; filtering data indicative of cardiac activity of the patient from the surrogate respiratory muscle pressure signal using the cardiac data received from an ECG sensor, if available; extracting a plurality of peaks in the filtered signal, the peaks corresponding to a shape of the filtered signal; and updating settings of a constrained optimization algorithm and/or a parametric optimization algorithm of the mechanical ventilator based on the shape-detected signal.

One advantage resides in improved monitoring for anomalies in patient respiratory effort during mechanical ventilation of a spontaneously respiring patient.

Another advantage resides in detecting an asynchrony in patient respiratory effort by filtering the cardiac activity of the patient from a respiratory signal.

Another advantage resides in detecting such an asynchrony in patient respiratory effort without determining the patient respiratory muscle pressure $P_{mus}(t)$.

Another advantage resides in automatically adjusting settings of a ventilator responsive to a detected asynchrony.

Another advantage resides in improving estimation of respiratory mechanics from constrained optimization/parametric optimization techniques by using the appropriate monotonicity constraints and timing of the true muscle pressure.

Further advantages of the present invention will be appreciated to those of ordinary skill in the art upon reading and understand the following detailed description. It will be appreciated that any given embodiment may achieve none, one, more, or all of the foregoing advantages and/or may achieve other advantages.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
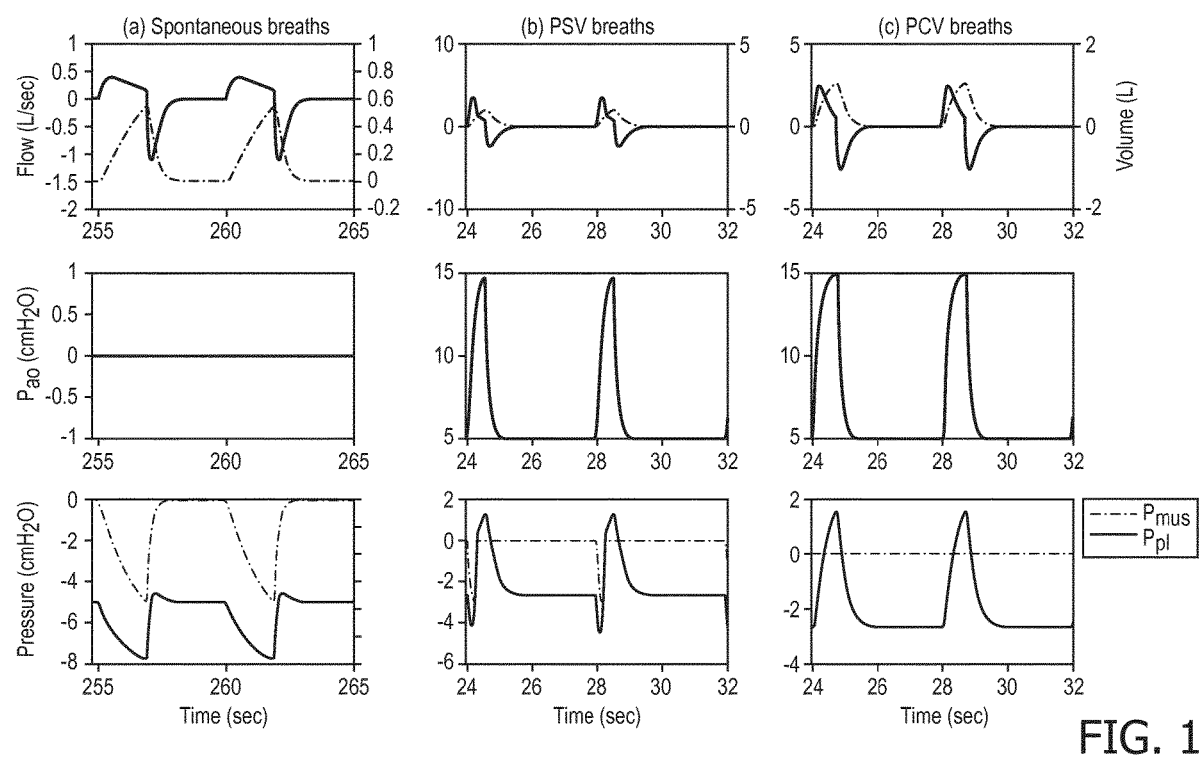
FIG. 1 shows several intrapleural pressure graphical profiles, $P_{pl}(t)$, with respect to the actual muscle pressure profiles, $P_{mus}(t)$, for different types of breaths.

In the following, improved respiratory system monitoring approaches are disclosed which leverage measured central venous pressure (CVP) to provide improved assessment of respiratory activity. In particular, the disclosed approaches recognize that CVP reflects the deflections caused by the activity of the respiratory muscles in the intrapleural pressure, $P_{pl}(t)$, which is the pressure in the thoracic cavity. More particularly, the right atrial pressure, $P_{ra}(t)$, correlates well with intrapleural pressure, $P_{pl}(t)$, and CVP is a surrogate for the right atrial pressure, $P_{ra}(t)$, as the CVP signal's measurement site is on the thoracic veins, located close to (right before) the right atrium. Cardiopulmonary modeling disclosed herein shows these relationships. Conceptually, the venous system (e.g. the superior and inferior vena cavae) return blood from the body into the right atrium, thus providing a physiological basis for relating $P_{ra}$ and CVP. Further, a relationship between intrapleural pressure, $P_{pl}(t)$ and respiratory muscle pressure, $P_{mus}(t)$, may be expressed (up to a constant term) as follows: $P_{mus}(t)=P_{pl}(t)-E_{cw} V_{air}(t)$ where $E_{cw}$ is the chest wall elastance and $V_{air}(t)$ is the lung inflation volume (computable as a time integral of airway air flow). In embodiments disclosed herein, this approximate relation is typically used, although it is contemplated to further account for secondary factors such as chest wall resistance and/or dependence of $E_{cw}$ on the lung inflation volume $V_{air}(t)$. Substituting CVP as a close proxy for the intrapleural pressure leads to the relationship of a surrogate muscle pressure $P_{mus, surr}(t)=CVP(t)-E_{cw} V_{air}(t)$. Advantageously, CVP is already monitored in many critical care settings as a component of cardiac and/or cardiovascular system monitoring in patients with cardiac or coronary ailments. By contrast, the intrapleural pressure $P_{pl}(t)$ and right atrial pressure $P_{ra}(t)$ are not typically monitored in critical care settings, and instruments for such monitoring are not readily available.

In some embodiments, the foregoing may be used to get a surrogate respiratory muscle pressure, $P_{mus,surr}(t)$, from measured CVP(t) and airway air flow. It will be appreciated that the surrogate muscle pressure signal that is computed using CVP may differ from the true $P_{mus}$ for all clinical conditions due to different factors, like cardiac activity, that affect the CVP waveform per se. In some embodiments, given the approximate nature of the underlying relationships, only the shape of the $P_{mus}(t)$ waveform is estimated from this relation—but this waveform shape information is recognized herein to be of significant value in improving respiratory system estimation in the presence of complicating factors such as patient-ventilator asynchrony. Hence, in embodiments described herein, CVP is used to get a surrogate muscle pressure signal ($P_{mus,surr}(t)$). This $P_{mus,surr}(t)$ signal is then used to get shape information and timing of the true $P_{mus}(t)$ signal. Subsequently, this information is used to modify already developed estimation techniques, e.g. CO and PO (these use airway pressure and air flow measurements only), so that the underlying true $P_{mus}(t)$ is more accurately estimated in the case of anomalous patient respiratory activity relative to the ventilatory support (asynchrony).

In general, approaches disclosed herein use measured CVP(t) to compute a surrogate $P_{mus}$ ($P_{mus,surr}$). In doing so, the signal (either CVP or $P_{mus,surr}$) is filtered to remove cardiogenic pulses due to the beating heart. The cardiogenic component may be identified using an external electrocardiogram (ECG) signal, or may be identified by analysis of the measured CVP(t) signal on the basis that the heart rate is a periodic signal with a typical frequency of 60-150 beats/min whereas respiration is typically on the order of 4-20 breaths/min. In some embodiments, the airway air flow and/or the CVP(t) signal is analyzed to segment breath intervals further assisting in the CVP and/or $P_{mus,surr}$ signal processing.

Physiological patient variables, like pressures, flows, heart rate and respiratory rate, can offer significant advances in the diagnosis and tracking of diseases. For instance, arterial blood pressure (ABP) of a patient is nearly ubiquitously monitored in hospitals and is indicative of the cardiac afterload and the stress developed in the ventricular wall. Another commonly measured signal is central venous pressure of a patient. CVP is primarily used by the medical community as an index of cardiac preload, which reflects the ability of the heart to generate sufficient pressure to induce blood flow. CVP offers an indication of the interaction between the cardiac function and the circulatory apparatus as portrayed by the well-known Frank-Starling curves. Therefore, CVP monitoring, in addition to the commonly measured ABP, is considered to offer physicians valuable insight on the dynamics of the cardiovascular apparatus, especially in the intensive care unit (ICU).

As recognized herein, in addition to the aforementioned cardiovascular-related information that physicians can attain when CVP monitoring is available at the bedside, the CVP waveform itself also demonstrates deflections that are associated with patient's respiratory activity. In particular, the thoracic veins, the site at which CVP is commonly measured, are located inside the thoracic cavity and thus are subject to the intrapleural pressure $P_{pl}$, which is the pressure between the lungs and the thoracic wall. As demonstrated herein by cardiopulmonary simulations, the intrapleural pressure exhibits prominent swings due to either spontaneous respiration (no external support) or external mechanical ventilation support. In the former case, the patient's respiratory effort, as expressed by muscle pressure ($P_{mus}$), the equivalent pressure of the force exerted by the respiratory muscles, pulls the diaphragm downwards and expands the thoracic wall, causing the $P_{pl}$ to decrease. During muscle relaxation, elastance of the chest wall, e.g. characterized by elastance parameter $E_{cw}$, causes intrapleural pressure to return to its resting value. In the case of a mechanically ventilated patient, for example in pressure control ventilation (PCV) mode, the mechanically ventilated patient shows $P_{pl}$ with positive swings that follow the delivered volume profile. Moreover, in partially-assisted mechanical ventilation modes, like in pressure support ventilation (PSV), where the patient and ventilator share the work performed on the respiratory apparatus, $P_{pl}$ contains both negative and positive swings depending on the balance between these two sources.

In simulation results reported herein, cardiopulmonary (CP) system modeling was used to demonstrate various relationships and correlations underlying the disclosed respiratory monitoring techniques utilizing CVP measurements. The CP model used for these simulations is described in Albanese et al., "An Integrated Mathematical Model of the Human Cardiopulmonary System: Model Development", *Am. J. Physiol.—Hear. Circ. Physiol.*, p. ajpheart.00230.2014, December 2015 (available online at http://www.ncbi.nlm.nih.gov/pubmed/26683899 or http://ajpheart.physiology.org/content/early/2015/12/14/ajpheart.00230.2014). This is an integrated cardiopulmonary model that mathematically describes the interactions between the cardiovascular and respiratory (i.e. pulmonary) systems along with their main short-term control mechanisms, and incorporates cardiovascular circulation, respiratory mechanics, tissue and alveolar gas exchange, and short-term neural control mechanisms acting on the cardiovascular and the respiratory functions. The CP system model can be utilized to simulate both normal CP behavior and CP behavior under the influence of various pathology conditions.

Sample simulated pressure and air flow waveforms for two consecutive breaths are depicted in FIG. 1. The effort exerted by an active (i.e., non-sedated) patient during spontaneous respiration or under PSV mode was simulated via $P_{mus}$ profiles that resemble the equivalent muscle pressure derived from experimental patient data. FIG. 1 illustrates that intrapleural pressure exhibits negative swings when the patient is active and positive deflections while the ventilator supports the delivery of air into the respiratory apparatus. $P_{ao}$ is the pressure at the patient's airway opening, or at the ventilator's Y-juncture, while flow and volume are indicative of the air flow being delivered to the lungs either due to the external ventilator support or due to the activity of the patient. It will be appreciated that volume is a direct integral of the flow and is reset to zero at a ventilator at the beginning of every breath.

As shown in FIG. 1, the steady state $P_{pl}$ has a negative value. At the end of each breath, the transpulmonary pressure (defined as alveolar pressure (i.e., inside) minus $P_{pl}$ (i.e., outside) pressure, needs to be positive in order for the lungs to be inflated (i.e., alveoli not collapsed). For instance, at a normal spontaneous breath, the transpulmonary pressure is around 5 $cmH_2O$ and since the airway pressure is zero, the pleural pressure $P_{pl}$ is equal to −5 $cmH_2O$. This end-expiratory pleural pressure $P_{pl}$ is thus associated to the Functional Residual Capacity (FRC) of the lungs and it is affected by the external (airway) end-expiratory pressure (PEEP). For instance, if PEEP value of PSV and PCV breaths is different than zero, the end-expiratory pleural pressure is larger than −5 $cmH_2O$.

Figure 2:
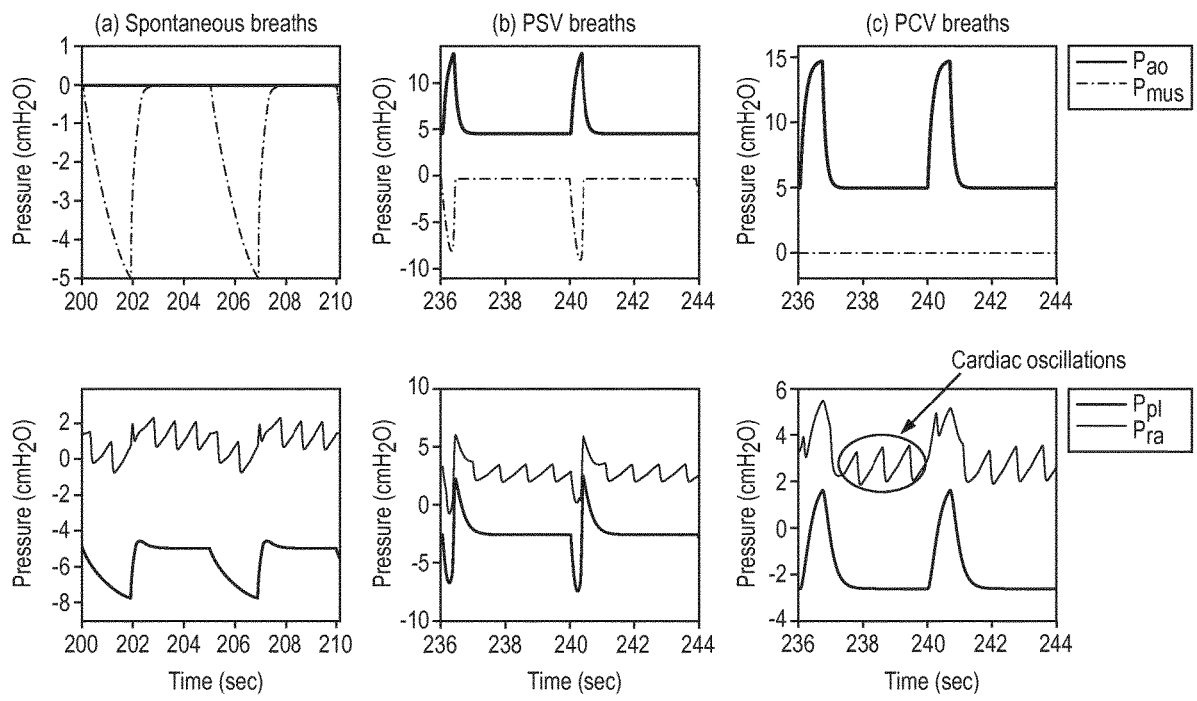
FIG. 2 shows several right atrial pressure profiles, $P_{ra}(t)$, ($P_{ra}$ is equivalent to CVP signal) in reference to the intrapleural pressure for the breaths shown in FIG. 1.

Referring to FIG. 2, a qualitative demonstration of the relationship between central venous and intrapleural pressure waveforms is attained by plotting these two signals along with $P_{mus}$. All signals are simulated for the different breath types shown in FIG. 1 (i.e., (a) spontaneous breaths, (b) PSV, and (c) PCV modes). In the simulation studies shown in FIG. 2, the right atrial pressure ($P_{ra}$) waveform instead of CVP is shown. Venous side catheterization (the catheter is sometimes referred to as central line catheter), which provides the CVP waveform in the clinical setting, aims to capture the dynamic behaviour of the right atrium and thus the measured CVP is expected to be a close proxy of $P_{ra}$. It will be appreciated that a CVP central line sensor is not the only way to obtain CVP signal information. Any means for such measurement are suitable to obtain CVP pressure values. Some CVP sensors are low pressure sensors and hence are prone to distortions in their outputs due to bulk patient movement In addition to the deflections caused by the respiratory activity, the right atrial pressure and thus the measured CVP waveform include cyclic oscillations pertaining to the cardiovascular function (i.e., the cardiogenic signal component, as indicated by the black circle in FIG. 2).

The CVP signal contains deflections due to dynamics arising either inside or outside the particular vessel or structure that serves as the measuring point. Cardiac oscillations are of the former type and are owing to the function of the heart and the circulatory apparatus. They can be attributed to the propagation of blood flow through the vasculature, back to the right side of the heart, or to wave deflections stemming from the contractile heart chambers (i.e., the right atrium and ventricle). Of the latter type, breathing patterns (either spontaneous or mechanically supported) affect the intravenous pressure by causing deflections whose magnitude and direction depend on the external intrapleural pressure and the vessel's stiffness.

Figure 3:
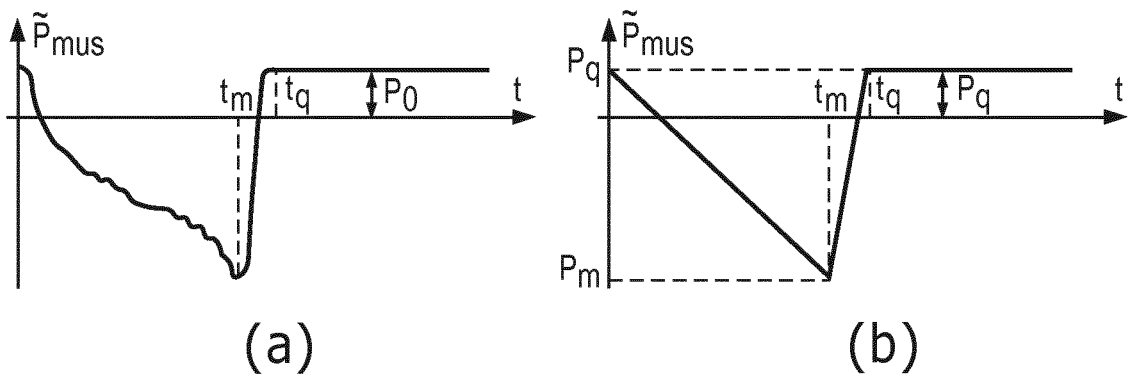
FIG. 3 shows candidate nominal (synchronous) $P_{mus}$ profiles subject to monotonicity constraints and linear piecewise constraints.

Algorithms, such as a constrained optimization (CO) algorithm and/or a parametric optimization (PO) algorithm, that estimate the respiratory apparatus mechanics (e.g., resistance, elastance, and the like) and the effort exerted by the patient's respiratory muscles (typically quantified as $P_{mus}$) by solving an Equation of Motion of the Lungs rely either on monotonicity constraints on the underlying respiratory muscle pressure $P_{mus}$ waveform, or on certain assumptions of a shape of the respiratory muscle pressure $P_{mus}$ profile, in order to overcome the typically underdetermined nature of the problem. For example, it can be assumed that, in a CO procedure, a $P_{mus}$ profile within a breath consists of a region of negative monotonicity, which extends up to the point with the minimum value, and a region of positivity monotonicity that is, in turn, followed by another region of constant pressure. For instance, a sample $P_{mus}$ profile that follows these monotonicity constraints is shown in the left hand graph of FIG. 3. In another example, such as a PO approach, it is assumed that $P_{mus}$ has morphological characteristics similar to CO but the piecewise regions follow certain pre-configured profiles, like linear (shown in the right-hand graph of FIG. 3), parabolic, or constant. PO searches over a range of possible $P_{mus}$ waveforms that differ in terms of shape, timing, and magnitude and selects the one that gives the optimal estimation results as far as the airway pressure fitting error is concerned.

Figure 4:
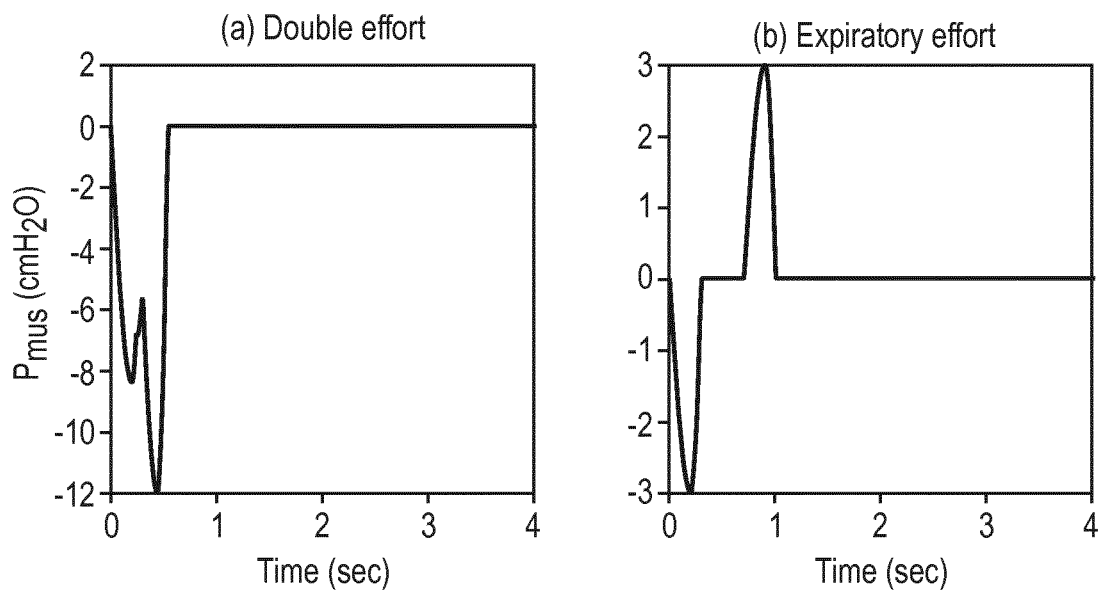
FIG. 4 shows a sample $P_{mus}$ profile for double inspiratory effort and expiratory effort.

The aforementioned assumptions on the morphological characteristics of $P_{mus}$ are satisfied for an appreciably large range of normal inspiratory effort profiles; however, there exist a significant number of cases, especially in diseased states and/or under poorly configured ventilator settings, where the muscle pressure does not comply with these constraints. Such cases could include, but are not limited to, double inspiratory efforts or forced expiratory efforts, similar to the ones shown in FIG. 4. Under these circumstances, the algorithmic performance of CO and PO is expected to degrade considerably. However, if the overall shape of the muscle pressure profile is known a priori, both algorithms can be modified accordingly and thus tailored to each particular breathing pattern. For instance, if a double inspiratory effort is detected, appropriate monotonicity, or piecewise, constraints can replace the default ones, so as to improve the estimation results not only in terms of $P_{mus}$, but also of the respiratory apparatus resistance and elastance estimates. To this end, information about the shape of $P_{mus}$ via the use of CVP measurements, as disclosed herein, can provide for a wider applicability of CO and PO estimation techniques within the clinical environment.

In another respiratory monitoring task, an accurate assessment of the initiation and termination of the patient's respiratory activity has been proved to be a major challenge. Proper and synchronous triggering and cycling off of each mechanically supported breath in accordance with the patient's demands can lead to benefits such as significant reduction of the work of breathing, shorter duration of hospitalization due to higher chances of weaning success and therefore lower healthcare costs. To this end, accurate detection of patient-ventilator asynchrony is desired. Conventionally, airway pressure and air flow measurements are used to determine the type and severity of the asynchrony and then provide the healthcare practitioner with appropriate corrective actions or automatically and optimally adjust relevant ventilator settings. In embodiments disclosed herein, the CVP waveform is also used for assessing asynchrony, as CVP provides a signal distinct from conventional respiratory measurements (e.g. airway pressure and flow) that reflects the intrapleural swings and hence the breathing effort.

As demonstrated by CP simulation results such as those described herein with reference to FIGS. 1 and 2, there is a correlative relationship between the intrapleural pressure ($P_{pl}$) and central venous pressure (CVP). In particular, various breathing patterns represented by the muscle pressure waveform across ventilation modes or patient conditions result in different intrapleural pressure waveforms, and thus correlated central venous pressure profiles. Based on this observation, the following advantageously provides a way, by using the CVP signal, to perform respiratory monitoring tasks such as: (1) appropriately modify the monotonicity constraints in a CO algorithm, or select the category of the pre-defined profiles of $P_{mus}$ in a PO algorithm; and (2) enhance the asynchrony detection and classification algorithms.

Figure 5:
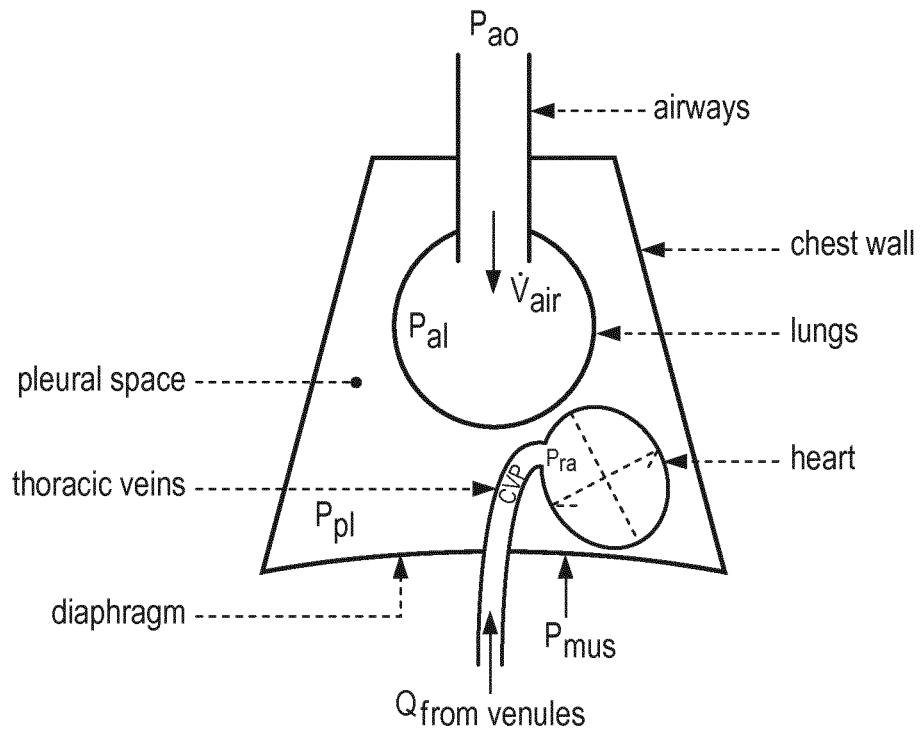
FIG. 5 shows a schematic representation of respiratory mechanics and the heart.

A schematic representation of the heart and lungs within the thoracic cavity is shown in FIG. 5. In this simplified figure, the respiratory apparatus (i.e. lungs) is represented by a single elastic alveolar compartment (i.e., balloon) with intra-alveolar pressure, $P_{al}$, and a resistive pathway (i.e., airways, e.g. the trachea). Both the alveoli and heart reside within the chest wall (i.e., thoracic cavity) and thus are subject to the intrapleural pressure, $P_{pl}$, which, in turn, depends on both the external airway pressure, $P_{ao}$, and the muscle pressure, $P_{mus}$. In the heart, the focus is drawn on the right atrium with pressure $P_{ra}$ that is filled with blood from the venules via the thoracic veins, primarily the superior and inferior vena cavae. As the right atrium is located inside the thoracic cavity, changes in the intrapleural pressure $P_{pl}$ impact the right atrial pressure $P_{ra}$, and vice versa. Because these pressure transfers depend on the elastic properties of the vascular tissue and the shape of the vessel, the value of the vessel's elastance indicates how attenuated these changes will be.

Figure 6:
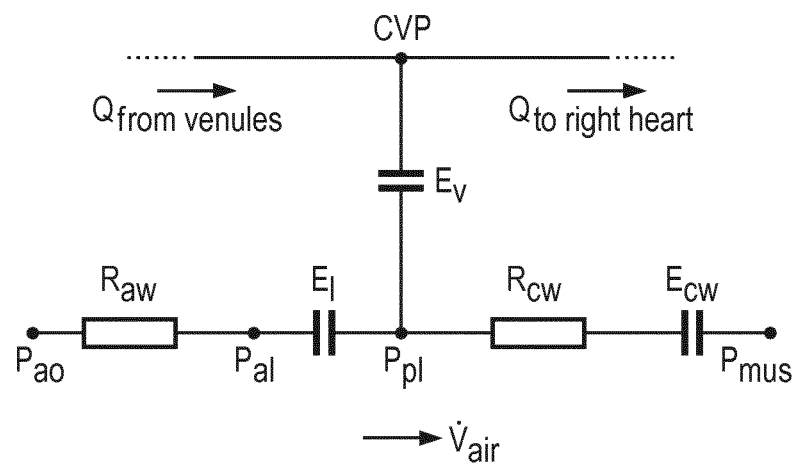
FIG. 6 shows an electrical analogue of the respiratory apparatus and central veins.

The electrical analogue corresponding to the above schematic representation is depicted in FIG. 6. The resistance and elastance elements of the airways/lungs are denoted as $R_{aw}$ and $E_L$ respectively, whereas the elastance of the chest wall is denoted as $E_{cw}$. The additional resistance, $R_{cw}$, that accounts for energy dissipation within the chest wall is often omitted due to the relatively low friction of the tissues. For instance, the CP model, used for the simulation results, neglects $R_{cw}$ and thus the intrapleural pressure is calculated as $P_{pl}=P_{mus}+E_{cw}V_{air}$, where $V_{air}$ is the volume of air delivered into the lungs and computed as the time integral of flow, $\dot{V}_{air}$ (a nominal value of $E_{cw}$ is 10 cmH$_2$O/L). CVP is the pressure within the thoracic (central) veins and $E_v$ is the parameter that reflects the elastic properties of the veins due to their material properties and geometry (i.e. shape).

According to the conservation of mass principle, the change in volume of the central venous compartment, as accounted for by the elastance element, $E_v$, is equal to the difference of the blood flow entering and exiting the corresponding spatial location. Hence, the following first-order ordinary differential equation (ODE) can be derived:

$$\frac{dV_{CVP}}{dt} = \qquad \text{Equation 1}$$
$$Q_{in} - Q_{out} \Rightarrow \frac{1}{E_v}(C\dot{V}P - \dot{P}_{pl}) = Q_{from\ venules} - Q_{to\ right\ heart}$$
$$\Rightarrow C\dot{V}P - \dot{P}_{pl} = E_v(Q_{from\ venules} - Q_{to\ right\ heart}).$$

One of the properties of the veins is their ability to act as a capacitance reservoir and store a significant amount of blood volume. This phenomenon is attributed to their high compliance value that depends on the state of venous tone and is altered by the sympathetic stimulation. It is then reasonable to assume that venous compliance is large, or $E_v \cong 0$ (a typical value for $E_v$ is 0.012 cmH$_2$O/L). Using this approximation, a surrogate signal for the intrapleural pressure can be derived, $$C\dot{V}P \cong \dot{P}_{pl} \Rightarrow \int_0^t C\dot{V}P(\tau)d\tau \cong \int_0^t \dot{P}_{pl}(\tau)d\tau \Rightarrow \qquad \text{Equation 2}$$
$$CVP(t) - CVP(0) \cong P_{pl}(t) - P_{pl}(0)$$
$$\Rightarrow P_{pl}(t) \cong CVP(t) - CVP(0) + P_{pl}(0).$$

As $P_{pl}$ is associated with the muscle effort via the chest wall mechanical properties (neglecting $R_{cw}$), it can then be deemed possible to express a surrogate $P_{mus}(t)$ signal by using the CVP(t) according to Equation 2, $$P_{mus}(t) = \qquad \text{Equation 3}$$
$$P_{pl}(t) - E_{cw}V_{air}(t) \overset{(2)}{\Rightarrow} P_{mus}(t) \cong CVP(t) - E_{cw}V_{air}(t) + P_0,$$
$$\text{where } P_0 = P_{pl}(0) - CVP(0) \text{ is a constant term.}$$

Equation 3 thus provides for calculation of a surrogate respiratory muscle pressure $P_{mus,surr}(t)$, or at least its waveform, given measured CVP(t) and $V_{air}(t)$, the latter being obtained as a time integral of airway air flow.

Figure 7:
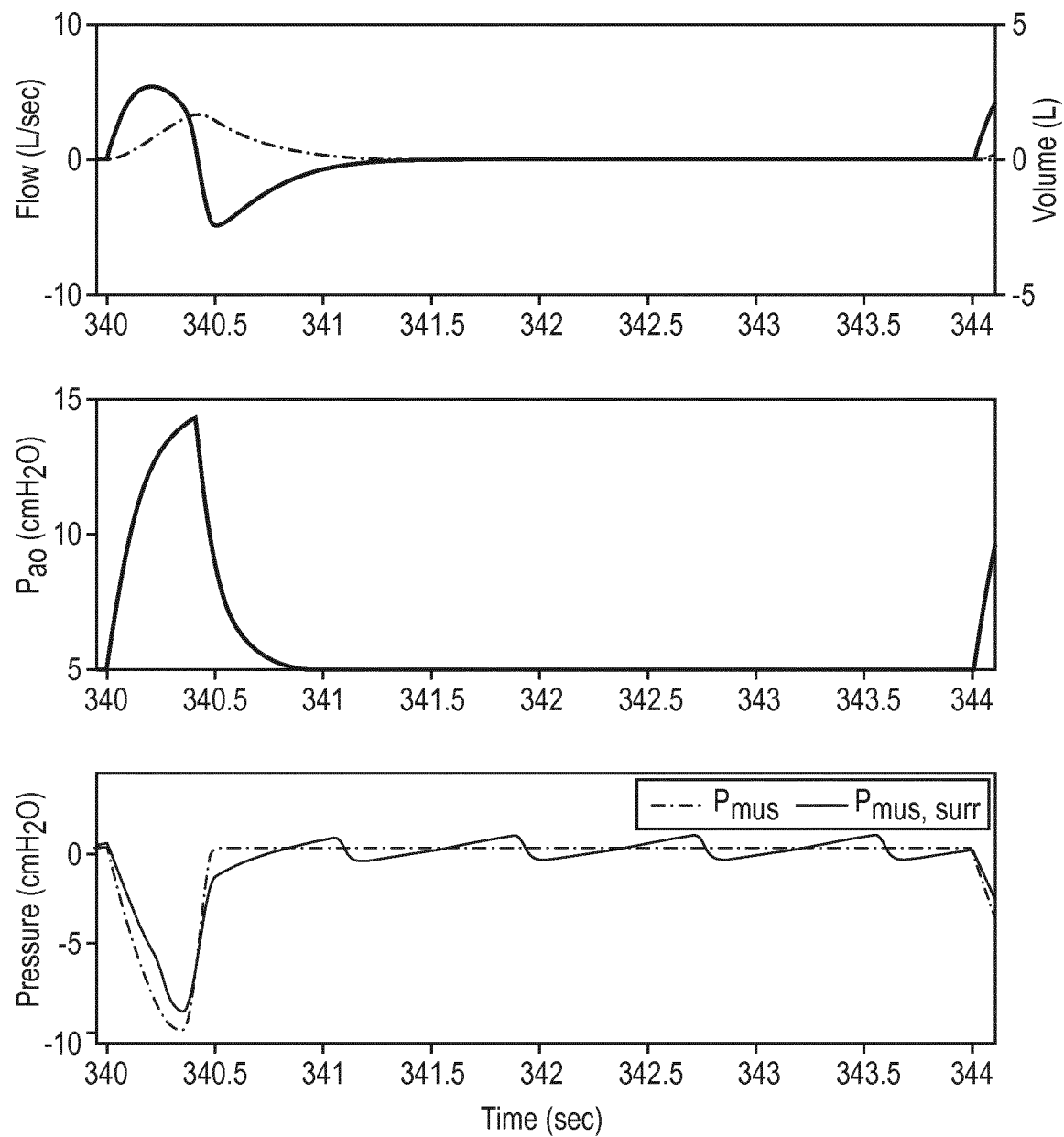
FIG. 7 shows actual and surrogate muscle effort signals during a regular inspiratory effort.
Figure 8:
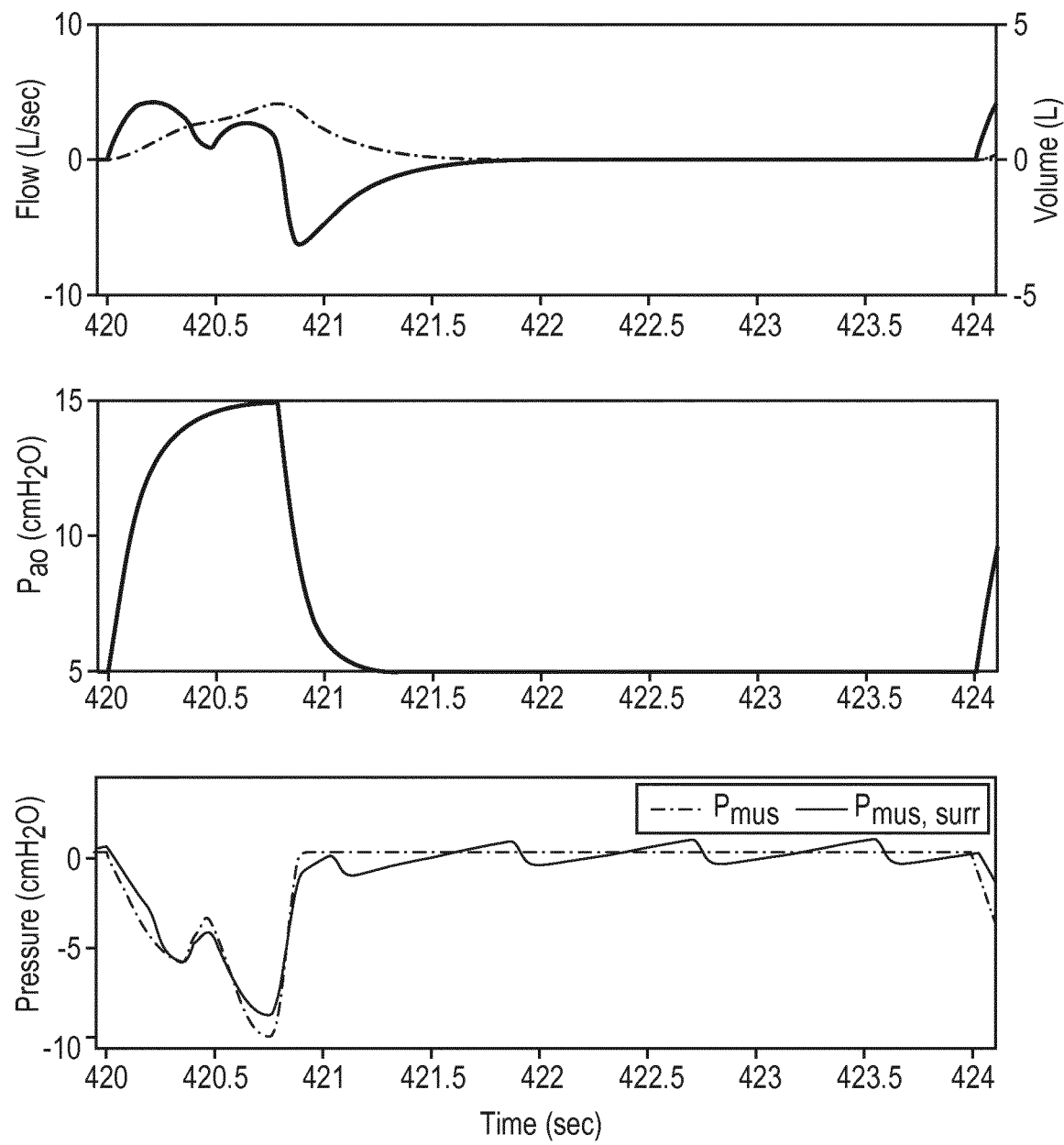
FIG. 8 shows actual and surrogate muscle effort signals during a double inspiratory effort.
Figure 9:
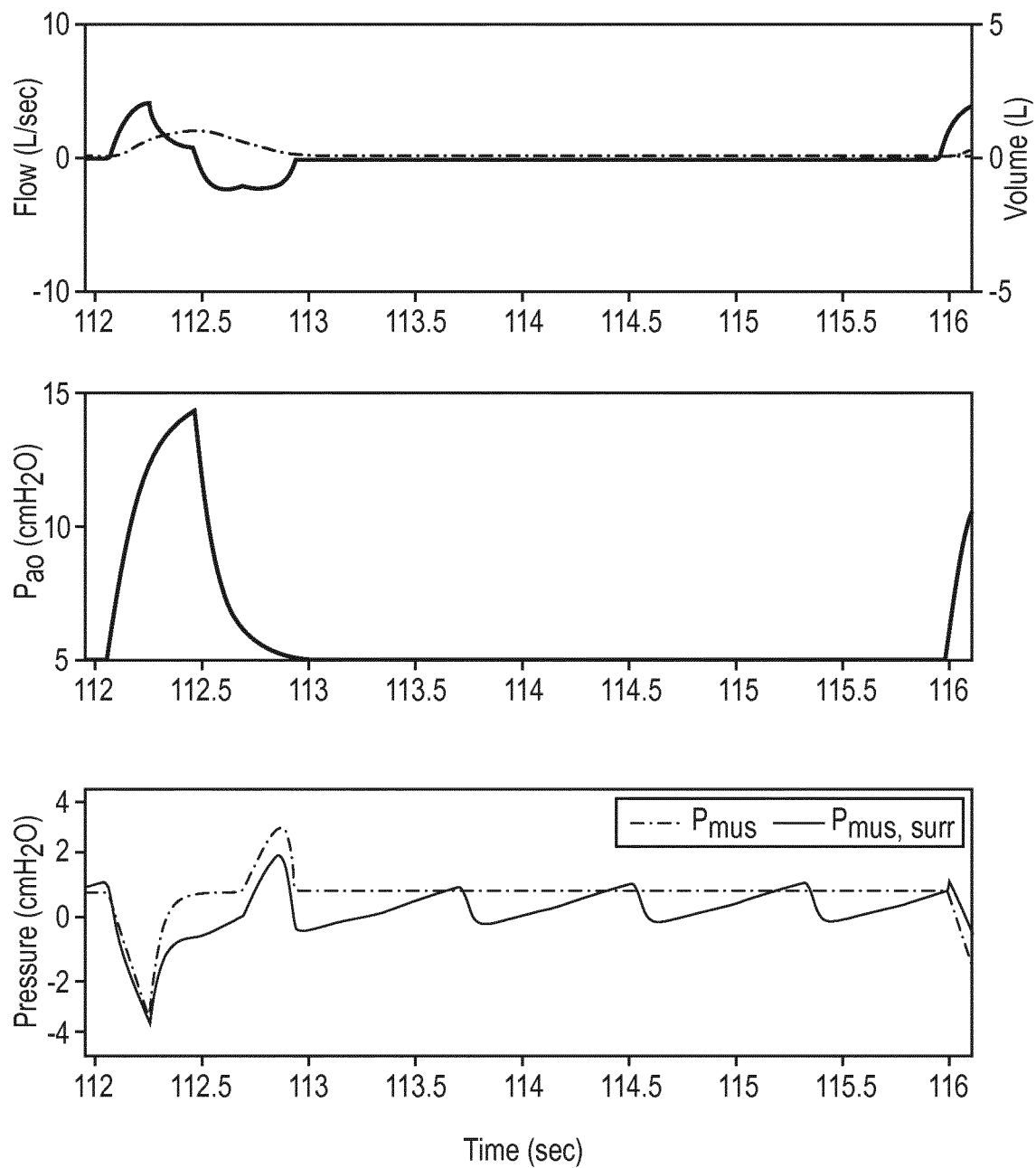
FIG. 9 shows actual and surrogate muscle effort signals during an expiratory effort.

For a visual comparison of the actual muscle pressure, $P_{mus}(t)$, and the surrogate signal $P_{mus,surr}(t)$ computed via Equation 3, i.e. $P_{mus,surr}(t) = CVP(t) - E_{cw}V_{air} + P_0$, PSV breaths are focused on, as pressure support ventilation is a common mode that allows the patient to actively breathe and share the work of breathing with the machine. It is thus expected that, during pressure support ventilation (PSV), the breathing patterns may significantly differ from breath to breath, based on the patient's clinical condition and the selected ventilator settings. Similarly to the simulation results presented earlier, a simplified version of a cardiopulmonary model can be used to generate $P_{mus}(t)$ and $P_{mus,surr}(t)$ and simulate the corresponding airway pressure, air flow, and volume waveforms for three different breathing patterns: (i) regular inspiratory effort (FIG. 7), (ii) double inspiratory effort (FIG. 8), and (iii) expiratory effort (FIG. 9). It will be appreciated that the CP model generates only the true $P_{mus}$ and then simulates/computes CVP, airway pressure and air flow signals. From this, the surrogate $P_{mus}$ is computed according to the assumption that $E_v$ is approximately zero. In FIGS. 7-9, the surrogate muscle pressure (i.e., the solid line in the bottom graph of each figure) computed via the central venous pressure (or the right atrial pressure in the case of the simulation studies presented herein) behave similarly to the actual $P_{mus}(t)$ (i.e., the dashed line in the bottom graph of each figure). One difference is that higher frequency oscillations are observed in the surrogate signal that are not present in the actual respiratory muscle pressure signal these higher frequency oscillations are cardiogenic oscillations due to the beating heart. The cardiogenic oscillations can significantly affect the derived surrogate signal $P_{mus,surr}(t)$ and it is thus desirable to be filtered out. Appropriate filtering could potentially include the use of electrocardiogram (ECG) signals for a more accurate identification of the cardiovascular-induced swings, or identifying the cardiogenic oscillations as periodic pulses in the CVP matching a known "reasonable" pulse rate range, e.g. 60-150 beats per minute in a typical healthy adult.

Although mechanical ventilation (MV) therapy has been used in the ICU for many years, it is still far from being optimal. Particularly, patient-ventilator asynchrony is one of the main issues associated with the use of MV in patients who are not completely sedated/paralyzed and are able to develop spontaneous respiratory efforts. Patient-ventilator asynchrony occurs when the timing of the ventilator cycle is not simultaneous with the timing of the patient's respiratory cycle. High levels of asynchrony are associated with increased work of breathing, longer duration of MV, higher incidence of tracheostomy, weaning failure, longer ICU length of stay and hospitalization, and hence increased healthcare costs and poor patient outcomes.

There are two classes of patient-ventilator asynchrony that can be further divided into a total of 5 different subtypes. Triggering asynchronies refer to a situation in which a beginning of the neural inspiratory period (neural Ti) does not match the beginning of the ventilator inspiratory period (mechanical Ti). Within this class, two subtypes of asynchrony can be identified: ineffective triggering and auto-triggering. Cycling off asynchronies refer to a situation in which the end of the neural Ti does not match the end of the mechanical Ti. Within this class, three subtypes of asynchrony can be identified: delayed cycling off early cycling off; and double triggering.

As used herein, the term "ineffective triggering" (and variants thereof) refers to a patient-ventilator asynchrony in which a patient initiates an inspiratory effort that fails to trigger the ventilator.

As used herein, the term "auto triggering" (and variants thereof) refers to a patient-ventilator asynchrony in which the ventilator is triggered without the presence of any voluntary inspiratory effort by the patient.

As used herein, the term "delayed cycling off" (and variants thereof) refers to a patient-ventilator asynchrony in which the ventilator cycles off (i.e. terminates the active delivery of pressure or flow) after the end of the neural Ti.

As used herein, the term "early cycling off" (and variants thereof) refers to a patient-ventilator asynchrony in which the ventilator cycles off (i.e. terminates the active delivery of pressure or flow) before the end of the neural Ti.

As used herein, the term "double triggering" (and variants thereof) refers to a patient-ventilator asynchrony in which the premature termination of the ventilator support generates the occurrence of a double inspiratory cycle within the same respiratory cycle.

Figure 10:
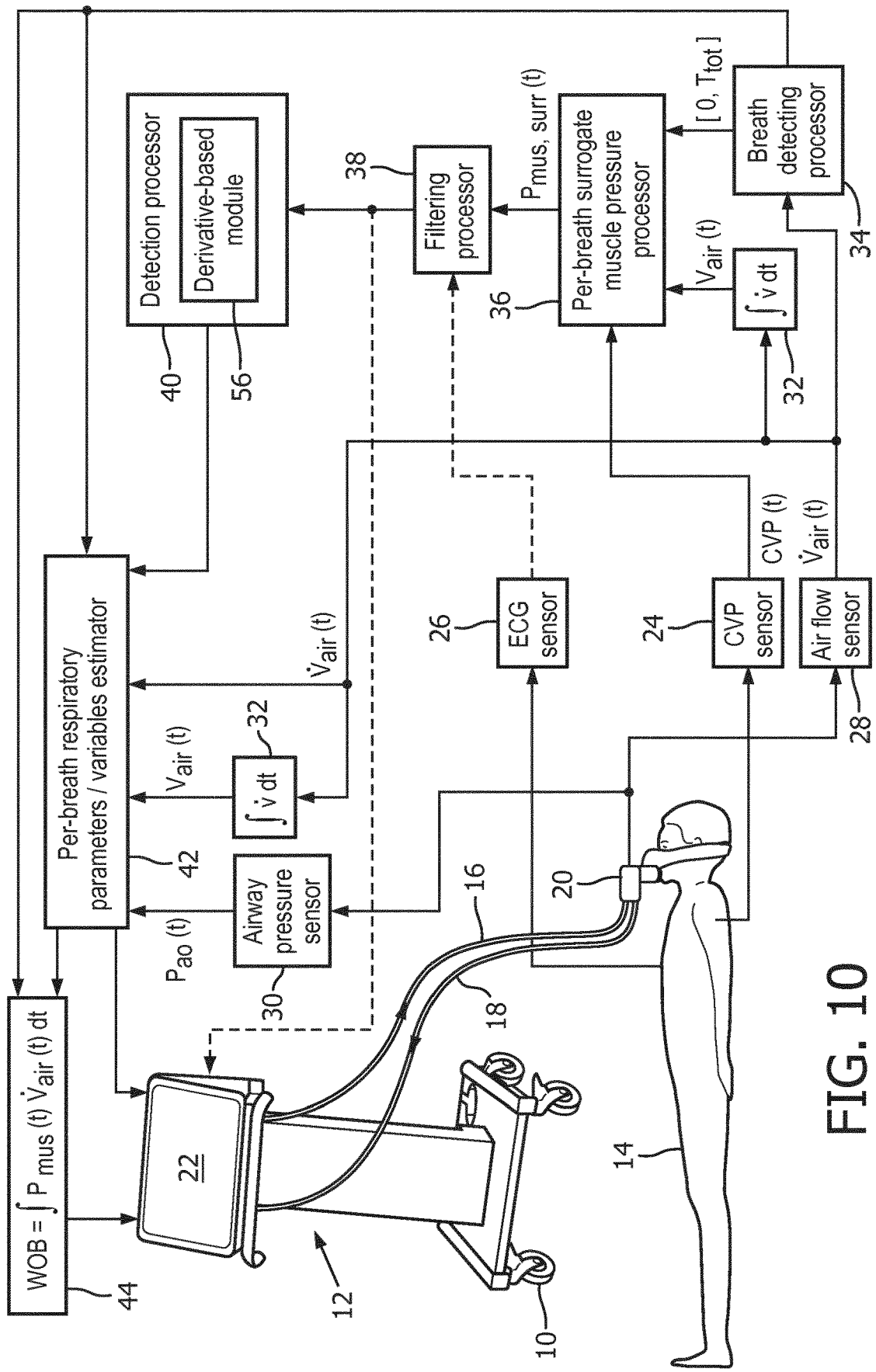
FIG. 10 shows a schematic of a proposed ventilator apparatus in accordance with one aspect of the present disclosure.

With reference to FIG. 10, an embodiment of a respiratory monitoring apparatus 10 is shown. In some embodiments, the respiratory monitoring apparatus 10 may include a mechanical ventilator 12 configured to deliver mechanical ventilation to a patient 14. Thus, the respiratory monitoring apparatus 10 may also be referred to as a mechanical ventilation apparatus.

The mechanical ventilation apparatus 10 is used to provide mechanical ventilation to a patient via the mechanical ventilator 12 that delivers air flow and/or pressure in accordance with ventilator settings to a ventilated patient 14 via an inlet air hose 16. Exhaled air returns to the ventilator 12 via an exhalation air hose 18. A Y-piece or T-piece 20 (or alternatively a tracheal tube, or in some cases a full-face mask) couples air from the discharge end of the inlet air hose 16 to the ventilated patient 14 during inhalation and couples exhaled air from the ventilated patient 14 into the exhalation air hose 18 during exhalation. Not shown in FIG. 10 are numerous other ancillary components that may be provided depending upon the ventilation mode and other therapy being received by the ventilated patient 14. Such ancillary components may include, by way of illustration: an oxygen bottle or other medical-grade oxygen source for delivering a controlled level of oxygen to the air flow, usually controlled by a Fraction of Inspired Oxygen ($FiO_2$) ventilator setting; a humidifier plumbed into the inlet line 16; a nasogastric tube to provide the patient 14 with nourishment; and so forth. The mechanical ventilator 12 has a user interface including, in the illustrative example, a touch-sensitive display 22 via which the physician, respiratory specialist, or other medical personnel can visualize the ventilator settings and monitor measured physiological variables (e.g., airway pressure and air flow) and operating parameters of the mechanical ventilator 12. Additionally or alternatively, the user interface may include physical user input controls (buttons, dials, switches, et cetera), a keyboard, a mouse, audible alarm device(s), indicator light(s), or so forth.

In addition, the patient 14 is monitored by a central venous pressure (CVP) sensor 24 configured to measure a CVP signal of the patient, an optional electrocardiogram (ECG) sensor 26 configured to measure an ECG signal of the patient, an airway flow sensor 28 configured to measure airway air flow as a function of time for the patient on the mechanical ventilator 12, and, an airway pressure sensor 30 configured to measure airway pressure as a function of time for the patient on the mechanical ventilator 12. The patient may be monitored by other sensors (not shown), such as a respiratory rate sensor, $SpO_2$ sensor, or so forth. Each of the illustrative sensors 24, 26, 28, 30 are described in more detail below.

The CVP sensor 24 is configured to measure a CVP signal of the patient 14. The CVP sensor 24 is inserted into a blood vessel, and more particularly a major vein, near the right atrium of the heart (i.e., the inferior vena cava). Advantageously, the pressure in the right atrium $P_{ra}$ is correlated with the pressure ($P_{pl}$) in the pleural cavity, between chest wall and lungs, of the patient and (together with the air flow) to the respiratory muscle pressure via Equation 3, and thus, the CVP pressure signal can be used to extract respiratory information of the patient 14. To do so, the respiratory monitoring apparatus 10 includes at least one processor that is programmed to generate respiratory information for the patient. For example, the illustrative at least one processor includes an integrating processor 32, a breath detecting processor 34, a per-breath surrogate muscle pressure processor 36, a filtering processor 38, a detection processor 40, a per-breath respiratory parameters/variables estimating processor 42, and a WOB calculator 44.

The integrating processor 32 computes the air volume $V_{air}(t) = \int \dot{V}_{air}(t)dt$. Further, because the approaches disclosed herein operate on a per-breath basis, the breath detecting processor 34 is configured to detect the onset of inspiration by analyzing the acquired air flow sample stream. Each successive breath is then defined as the interval from the onset of one inspiration period to the onset of the next inspiration period. Each breath identified by the breath analyzer spans a time interval $[0, T_{tot}]$ where time 0 corresponds to the first sample at the onset of the inspiration period and time $T_{tot}$ corresponds to the end of the breath, that is, the last sample just before the beginning of the next breath. The per-breath surrogate muscle pressure processor 36 is programmed to receive: (1) the CVP signal from the CVP sensor 24; and (2) the volume of air from the integrating processor 32. For each breath interval $[0, T_{tot}]$ delineated by the breath detecting processor 34, the per-breath surrogate muscle pressure processor 36 is programmed to segment the CVP and air volume signals into breath intervals (i.e., individual breaths) and calculate the surrogate muscle pressure signal, $P_{mus,surr}(t)$, as a function of time using Equation 3 (reproduced here):

$$P_{mus,surr}(t) = CVP(t) - E_{cw}V_{air}(t) + P_0$$

where t belongs to the breath interval $[0, T_{tot}]$, $CVP(t)$ denotes the CVP signal, $E_{cw}$ denotes a chest wall elastance, $V_{air}$ denotes a lung air volume computed by the integrating processor 32, and $P_0$ corresponds to a constant. Determination of the bias term $P_0$ is not of importance as the true muscle pressure signal is always shifted in order to start from, and end to, a zero value. In addition, in applications for which the $P_{mus}$ waveform shape is of interest (for example to identify monotonically increasing or decreasing regions, double-peaks, or other such dynamic structure), the choice of $P_0$ value is not of significance.

Figure 11A:
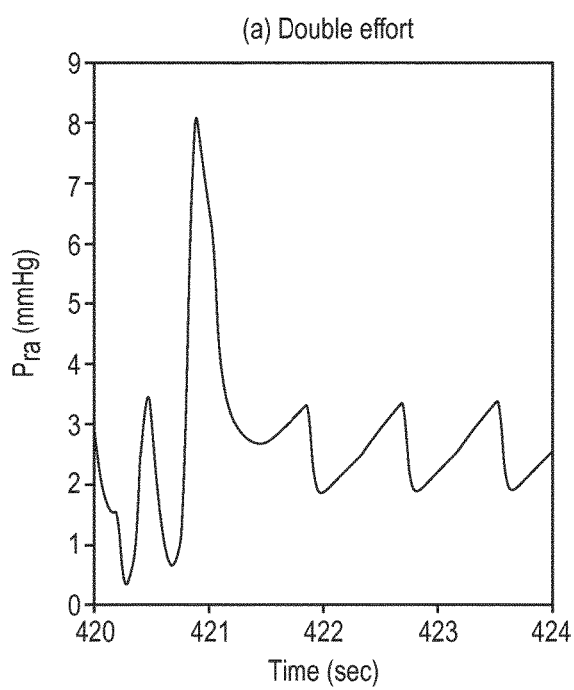
FIG. 11A shows a graph of right atrial pressure corresponding to a breath with double inspiratory effort.
Figure 11B:
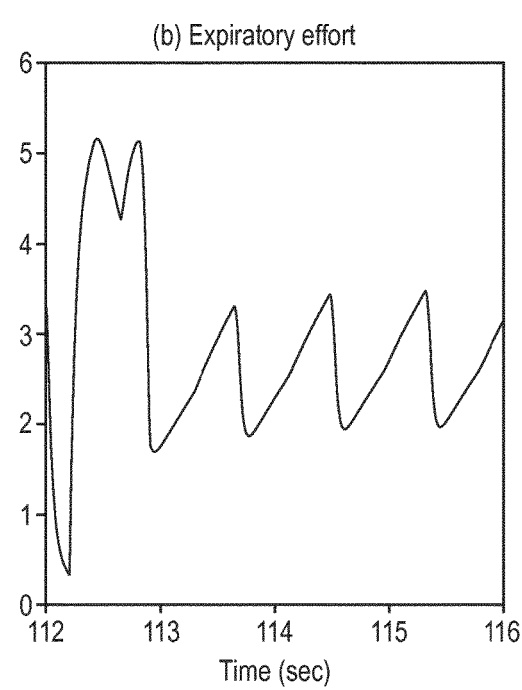
FIG. 11B shows a graph of right atrial pressure corresponding to a breath with expiratory effort.

The per-breath $P_{mus,surr}$ signal is then transmitted to the filtering processor 38. At this point, the segmented CVP and/or $P_{mus,surr}$ signal could also be displayed on a display 22 of the respiratory monitoring apparatus 10. FIG. 11A shows the segmented CVP signal displayed on the display 22 for a breath with double inspiratory effort, while FIG. 11B shows the segmented CVP signal displayed on the display 22 for a breath with expiratory effort. In both FIGS. 11A and 11B, the right atrial pressure $P_{ra}$ (suitably represented by CVP) has been segmented with the time samples given by the breath detector 34.

The filtering processor 38 is programmed to receive the per-breath $P_{mus,surr}$ signal from the per-breath surrogate muscle pressure processor 36. In some embodiments, when the ECG sensor 26 is included, the filtering processor 38 is also programmed to receive an ECG signal from the ECG sensor 26, and segment the ECG signal into breath intervals according to the output of the breath detector 34. The filtering processor 38 is programmed to filter the received $P_{mus,surr}$ signal to remove a cardiac activity component of the signal. In some embodiments, when the ECG sensor 26 is not used, the filtering processor 38 is programmed to remove data from the $P_{mus,surr}$ signal indicative of cardiac activity of the patient 14. For example, cardiogenic oscillations in $P_{mus,surr}$ signal are expected to be substantially periodic in nature with a frequency much higher than the respiratory rate. Thus, the filtering processor 38 can determine which portions of the $P_{mus,surr}$ signal to filter out. In another example, when the ECG sensor 26 is used, the filtering processor 38 is programmed to use the received ECG signal to filter (i.e., "remove") the portions of the $P_{mus,surr}$ signal that are indicative of cardiac activity of the patient. In a variant embodiment, the cardiogenic component can be filtered out from CVP signal first followed by the computation of the surrogate muscle pressure signal.

Figure 12A:
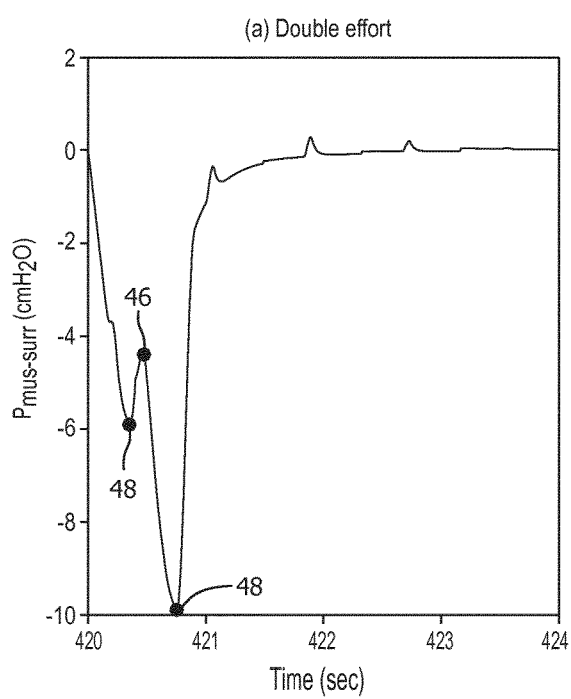
FIG. 12A shows a graph of filtered surrogate muscle pressure profiles along with peak detection for a breath with double inspiratory effort.
Figure 12B:
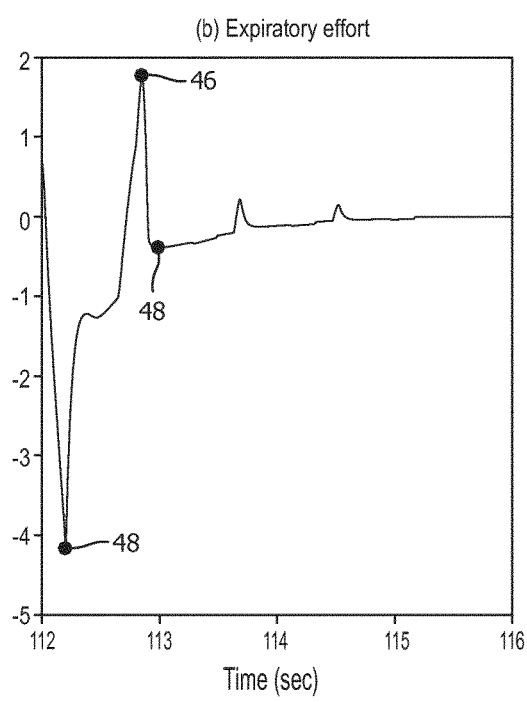
FIG. 12B shows a graph of filtered surrogate muscle pressure profiles along with peak detection for a breath with expiratory effort.

At this point, the filtered $P_{mus,surr}$ signal could be displayed on the display 22. FIG. 12A shows the surrogate $P_{mus}$ signal displayed on the display 22 for a breath with double inspiratory effort, while FIG. 12B shows the surrogate $P_{mus}$ signal displayed on the display 22 for a breath with expiratory effort. In both FIGS. 12A and 12B, the $P_{mus,surr}$ signal computed by Equation 3 has been filtered to remove the cardiac components of the surrogate signal; small peaks, e.g. at about 421 sec, 422 sec, and 423 sec in FIG. 12A, are residual cardiogenic signal remaining after the filtering.

It will be appreciated that the generated respiratory information for the patient 14 can include: (1) a surrogate intrapleural pressure signal equated to the segmented and filtered CVP signal (i.e., the segmented and filtered CVP signal value, see Equation 2); (2) a filtered surrogate respiratory muscle pressure waveform determined for each breath interval from the segmented CVP signal (i.e., $P_{mus, surr}$, see Equation 3); and the like (e.g. WoB or PoB). Each of the generated respiratory information can, in some embodiments, be displayed on the display 22.

In some embodiments, the detection processor 40 is programmed detect or extract features of the calculated surrogate $P_{mus}$ signal to determine a shape of the signal. For example, the detection processor 40 is programmed to detect a plurality of peaks 46 and 48 in the segmented and filtered $P_{mus,surr}$ signal. From the detected peaks 46 and 48, the detection processor is programmed to generate the respiratory information (e.g., CVP(t), $P_{mus,surr}$(t), and the like) segments over time intervals delineated by the peaks. The peaks 46 correspond to the positive peaks, and the peaks 48 correspond to negative peaks. The detection processor 40 is programmed to identify the positive peaks 46, the negative peaks 48, and the monotonicity of the segments between the peaks, i.e., segments with negative monotonicity 50, with positive monotonicity 52 and constant value 54. The shape of the surrogate $P_{mus}$ signal can be used to alter constraints or parameters in a corresponding CO algorithm and/or a PO algorithm incorporated in a per-breath respiratory parameters/variables estimating processor 42. For example, the physiological knowledge of the shape of the muscle pressure profile can be infused in the respiratory parameters/variables estimating processor 42 in the form of regional constraints on $P_{mus}$(t). In the CO approach, such monotonic regions are expressed in a set of inequalities and equalities and the desired respiratory system parameters and $P_{mus}$(t) profile are estimated by a constrained optimization problem whose quadratic cost function is subject to the aforementioned regional constraints. In a different aspect, a PO approach employs simple yet realistic mathematical templates to express the linear piece-wise parameterized $P_{mus}$(t) over a single breath. The WOB calculator 44 is programmed to process the per-breath estimated $P_{mus}$(t) from the estimator 42 and programmed to compute a value for the patient's Work of Breathing (or Power of Breathing) according to the equation WOB=$\int P_{mus}(t)\dot{V}(t)dt$ (or POB=$1/T\int_0^T P_{mus}(t)\dot{V}(t)dt$, where T is some chosen time interval preferably encompassing several breaths).

Figure 13A:
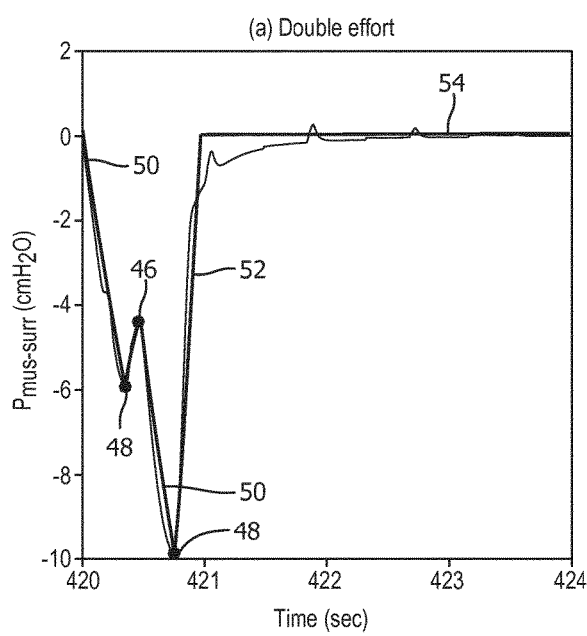
FIG. 13A shows segments of surrogate muscle pressure signal with positive monotonicity, negative monotonicity, and constant value for the filtered signal of FIG. 12A.
Figure 13B:
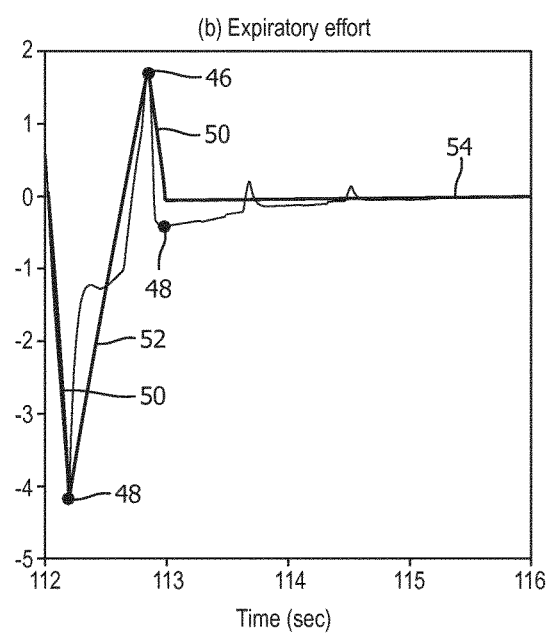
FIG. 13B shows segments of surrogate muscle pressure signal with positive monotonicity, negative monotonicity, and constant value for the filtered signal of FIG. 12B.

For example, the detection processor 40 can include any suitable peak detection hardware (e.g., a peak detector circuit with a diode and a capacitor) or software (e.g., a Matched Filtration with Experimental Noise Determination algorithm, a vectorized peak detection algorithm, a least-squares curve-fitting algorithm, an optimization peak detection algorithm, a derivative-based algorithm, or the like). In illustrative embodiments described herein, the detection processor 40 uses a derivative-based module 56 to detect peaks of $P_{mus,surr}$(t) versus time signal. It will be appreciated that the derivative-based module 56 also includes any suitable algorithms for signal processing processes (e.g., filtering, signal to noise ratio reduction, data smoothing, and the like). As described in more detail below, the derivative-based module 56 is configured to identify one or more anomalies in the breathing pattern based on the peak detection readings, as described in more detail below. The derivative-based module 56 is configured to detect peak values 46, 48 (e.g., "y-axis" values of the $P_{mus,surr}$(t) versus time signal, as described in more detail below) and the associated time values (e.g., "x-axis values") at which these peaks occur. From the peaks 46, 48, the shape of the $P_{mus,surr}$ signal can be determined. The detected segments of distinct monotonicity for the $P_{mus,surr}$(t) signals are shown in FIGS. 13A and 13B for a breath with double inspiratory effort (FIG. 13A) and a breath with expiratory effort (FIG. 13B).

Figure 14:
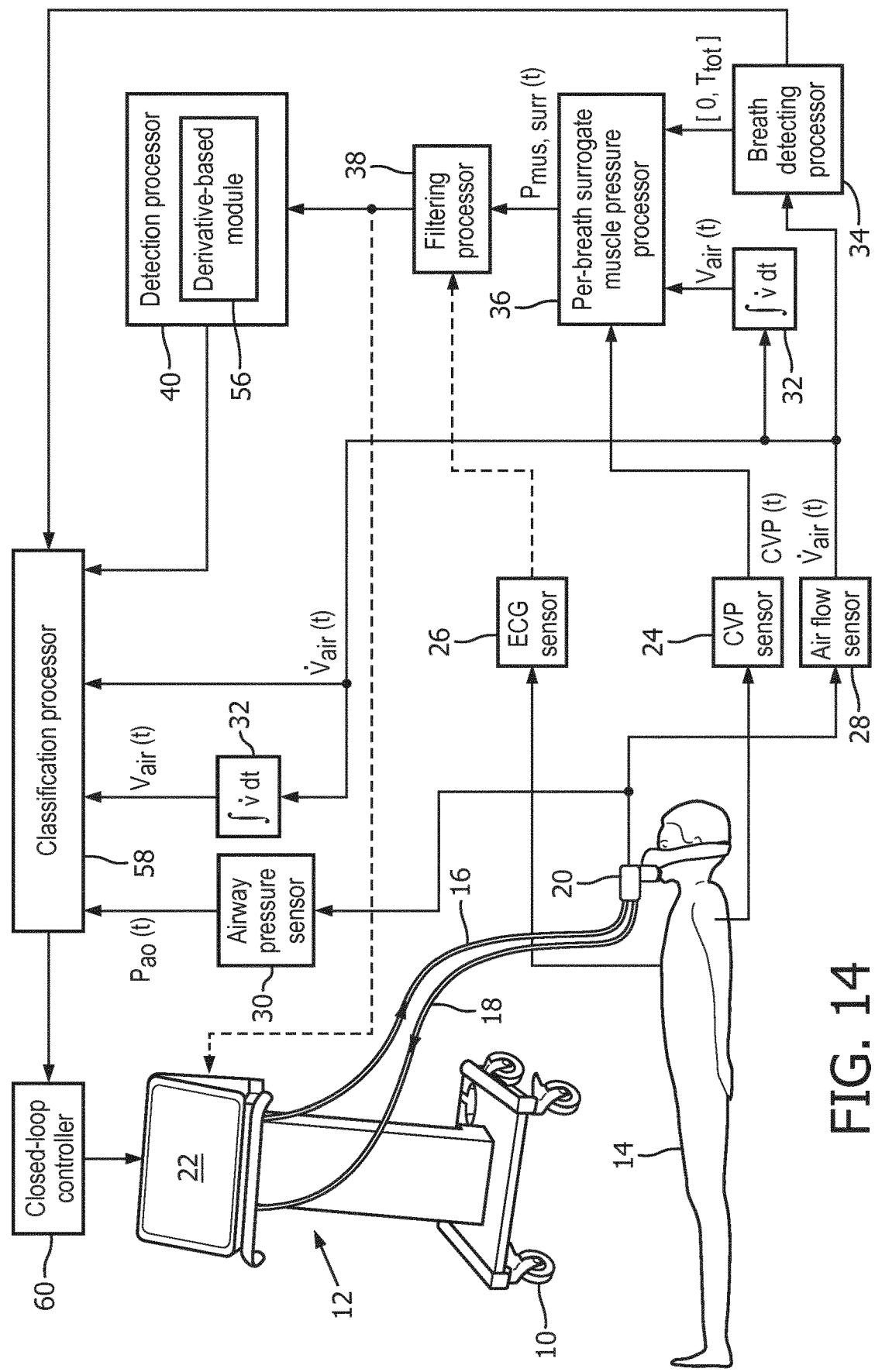
FIG. 14 shows a schematic of a proposed ventilator apparatus in accordance with another aspect of the present disclosure.

FIG. 14 shows another embodiment of the mechanical ventilation apparatus 10', in which the respiratory information derived at least in part from CVP measurements is used to provide open-loop ventilator control guidance or automated closed-loop ventilator control. The mechanical ventilation apparatus 10' can be configured substantially identically to the mechanical ventilation apparatus 10 of FIG. 10, except as described below.

The mechanical ventilation apparatus 10' includes the mechanical ventilator 12 (and associated components), the CVP sensor 24, the optional ECG sensor 26, the air flow sensor 28, the airway pressure sensor 30, the integrating processor 32, the breath detecting processor 34, the per-breath surrogate muscle pressure processor 36, the filtering processor 38, the detection processor 40, the per-breath respiratory parameters/variables estimating processor 42, and the WOB calculator 44, and the display 22, as described above. The mechanical ventilation apparatus 10' also includes a classification processor 58, which is described in more detail below.

As described above, the integrating processor 32 computes the time integral of the air flow and the breath detecting processor 34 identifies the onset of the inspiration and defines the breath interval $[0, T_{tot}]$ for each breath. The per-breath surrogate muscle pressure processor 36 is programmed to receive the CVP signal from the CVP sensor 24, the air volume from the integrator 32, and the breath interval from the breath detecting processor 34. The processor 36 is programmed to segment the CVP and volume signals using the breath interval time instances and compute the per-breath surrogate muscle pressure signal, as described above.

The per-breath $P_{mus,surr}$ signal is transmitted to the filtering processor 38, where it is being filtered as described above. An optional ECG signal from the ECG sensor 26 can also be used by the filtering processor 38 to improve the filtering process. The filtered per-breath $P_{mus,surr}$ signal is then processed by the detection processor 40 to determine the peaks 46, 48 thereof. These peak-detected signals could be displayed on the display 22. The peak-detected signal is also transmitted to the classification processor 58.

Figure 15:
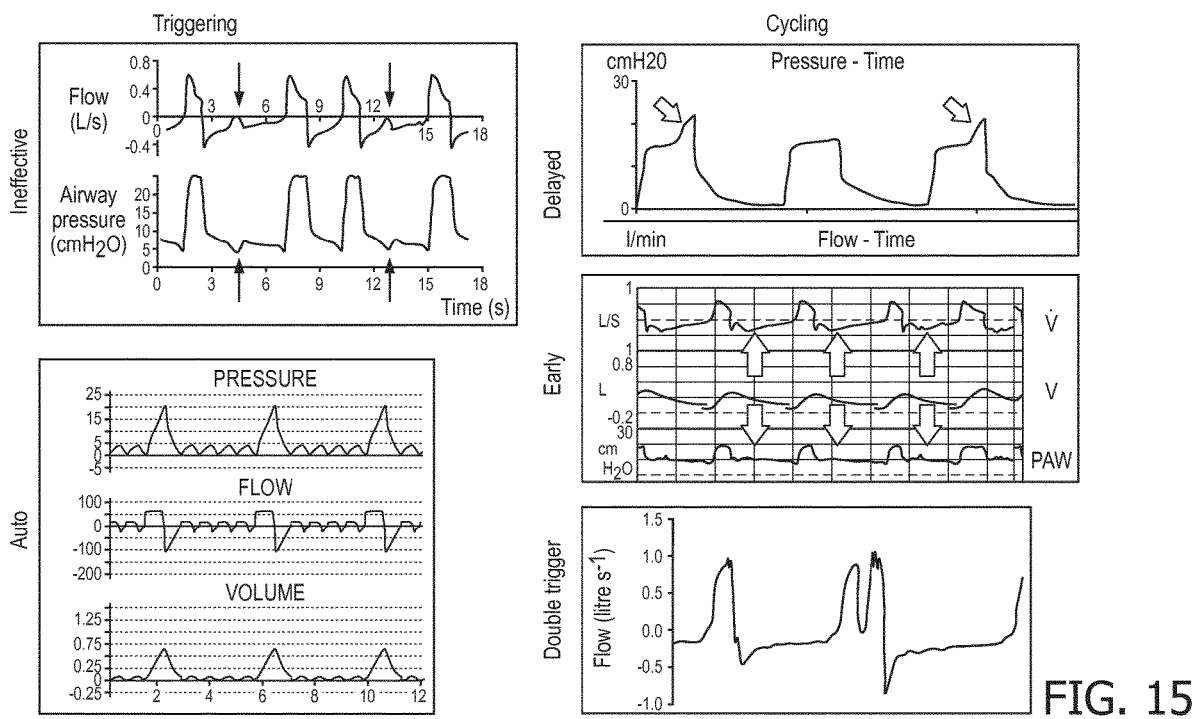
FIG. 15 shows example graphs of different type of patient-ventilator asynchronies.

The classification processor 58 is programmed to classify in a per-breath basis an asynchrony based on the extracted (i.e., peak-detected) $P_{mus,surr}$ signal, the airway pressure, air flow, and volume signals according to at least one of: no asynchrony; ineffective triggering; auto-triggering; delayed cycling off; early cycling off; and double triggering. FIG. 15 shows examples of a displayed signal for each type of asynchrony. The classification processor 58 can be configured as an artificial neural network, a Logistic Regression algorithm, a Bayes classification algorithm, and the like.

Referring back to FIG. 14, the classification processor 58 is configured to receive peak and monotonicity detection readings from the derivative-based module 56 of the detection processor 40. From these peak and monotonicity detection readings, the classification processor 58 is configured to indicate any anomalous/abnormal breath and determine the type of patient-ventilation asynchrony (e.g., ineffective triggering; auto-triggering; delayed cycling off; early cycling off; and double triggering). The classification processor 58 then "flags" the asynchrony, and can assign a corresponding indication to the type of asynchrony, as described in more detail below. The indication is then transmitted to, and displayed on, the display 22.

The classification processor 58 then analyzes the extracted surrogate muscle pressure signal from the detection processor 40 along with airway pressure, air flow, and volume waveforms to determine a type of asynchrony. In the example shown in FIGS. 13A and 13B, the filtered surrogate muscle pressure signal includes multiple peaks, either positive 46, or negative 48, and different regions of distinct monotonicity, like negative 50, positive 52, or constant value 54. By using the signals shown in FIG. 15 as a "template", the classification processor 58 can compare the templates to the actual measured signals of airway pressure and air flow, and/or use the positions of the peaks 46, 48 and segments of distinct monotonicity 50, 52, 54 in surrogate muscle pressure signal to determine the type of asynchrony. Due to the positioning of the negative and positive peaks 46 and 48 (described above), the classification processor 58 determines that the underlying muscle pressure effort is subject to double inspiratory effort (FIG. 13A) or expiratory effort (FIG. 13B). The classification processor 58 then flags the asynchrony type, for instance a possible double triggering asynchrony for FIG. 13A and a delayed cycling off asynchrony for FIG. 13B, and sends the indication of the asynchrony (i.e., a numerical value) to the display component 22, where it is displayed for a medical professional (e.g., a nurse, a doctor, and the like).

In other embodiments, when an asynchrony is detected, the indication and/or the displayed signal of $P_{mus,surr}(t)$ conveys to a medical professional that the asynchrony is occurring. The classification processor 58 is further programmed to suggest a recommendation for a medical professional to adjust the settings of the mechanical ventilator 12 to correct the asynchrony. The recommendation is displayed on the display 22. The medical professional can then adjust the settings of the ventilator 12 so that the asynchrony no longer occurs. In this manner, the mechanical ventilation apparatus 10' is an open-loop apparatus. A summary of suitable corrective action(s) for each type of asynchrony is described in Table 1 below.

TABLE 1

| Asynchrony Type | Corrective Action |
| --- | --- |
| Ineffective triggering | 1. Decrease trigger threshold<br>2. Reduce sedation<br>3. Reduce the potential for intrinsic PEEP:<br>Decrease tidal volume;<br>Decrease pressure support; |

TABLE 1-continued

| Asynchrony Type | Corrective Action |
| --- | --- |
| | Increase exhalation time;<br>Reduce resistance in airways |
| Auto-triggering | 1. Increase trigger threshold<br>2. Switch from flow to pressure triggering<br>3. Check for circuit leaks |
| Delayed cycling off | 1. Increase cycling threshold<br>2. Decrease Ti |
| Early cycling off | 1. Increase Ti<br>2. Decrease cycling threshold |
| Double triggering | 1. Increase tidal volume<br>2. Increase sedation<br>3. Increase Ti<br>4. Decrease cycling threshold |

In further embodiments, the mechanical ventilation apparatus 10' is further programmed to automatically adjust the settings of the mechanical ventilator 12 to correct the asynchrony. To do so, the mechanical ventilation apparatus 10' includes a closed-loop controller 60. In some embodiments, the closed-loop controller 60 can be configured as a power of breathing or a work of breathing controller. In such case, integrated into the controller 60 are the per-breath respiratory parameters/variables estimating processor 42 and the WOB/POB calculator 44. The closed-loop controller 60 is programmed to calculate the patient's power (or work) of breathing by time integration of the product of the estimated $P_{mus}(t)$ from 42 and air flow and to adjust the ventilator setting based on the difference between the actual and desired power or work of breathing in order to optimally support the patient's spontaneous respiratory effort. Such a closed-loop controller is described in U.S. Patent Publication No. 2015/0059754, which is incorporated in its entirety herein. In embodiments disclosed herein, the indication output by the classification processor 58 is also input to the closed-loop ventilator controller 60. If the indication indicates a respiratory asynchrony, then the closed loop ventilator controller 60 can take appropriate action, such as maintaining the current ventilator setting in an open-loop fashion, or adjusting ventilator settings based on the detected asynchronous condition, based on the recommendations listed in Table 1. In other embodiments, the controller 60 can be a multiple-input and multiple-output (MIMO) controller that accepts, besides the WOB/POB value, additional physiological variables, such as $SpO_2$, end-tidal $CO_2$, and/or mean arterial blood pressure values, and accordingly adjusts multiple ventilator settings, like the pressure support level, the end-expiratory pressure, the triggering and cycling-off sensitivity, and/or the fraction of oxygen in the supplied air.

It will also be appreciated that the various signals and values described herein can be communicated to the various processors 36, 38, 40, 58 and components 12, 22, 42, 44, 60 via a communication network (e.g., a wireless network, a local area network, a wide area network, a personal area network, BLUETOOTH®, and the like). Alternatively, the components 36, 38, 40, 42, 44, 58 and controller 60 may be built into the mechanical ventilator 12 (e.g., executing on a microprocessor or microcontroller of the ventilator 12) in which case data from the sensors 24, 26, 28, 30 are collected by the ventilator 12 and hence available to the components 36, 38, 40, 42, 44, 58 and controller 60. In another contemplated embodiment, the algorithms of the processors are implemented on the microprocessor of a patient monitor (not shown) that displays vital signs such as heart rate, respiration rate, blood pressure, or so forth, and the output of these processors 36, 38, 40, 58 and components 42, 44 are suitably displayed on the patient monitor display component.

Figure 16:
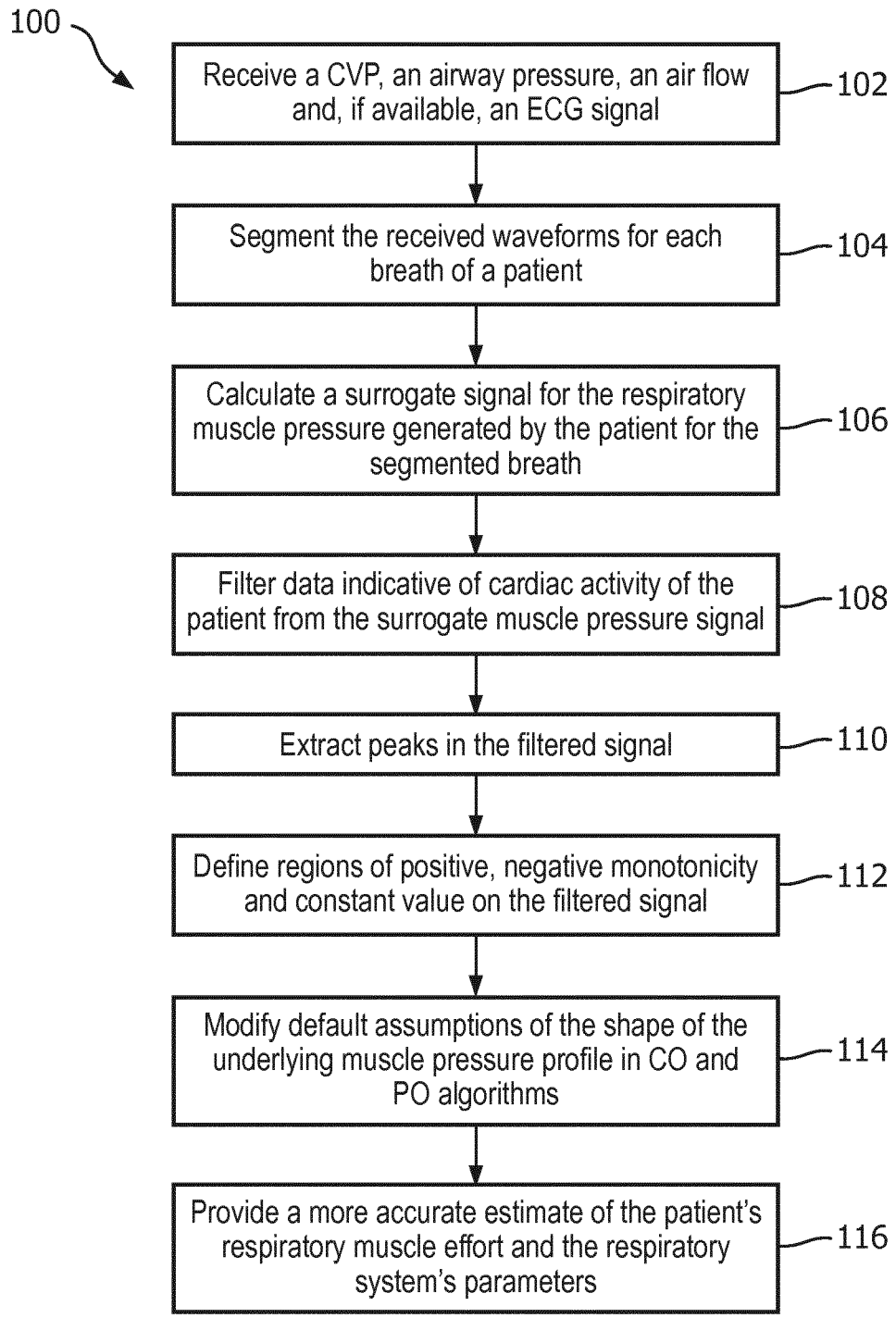
FIG. 16 shows a flow chart of an exemplary method of use for the ventilator apparatus of FIG. 10.

FIG. 16 shows a method 100 of improving the respiratory parameter estimation in the case of an anomalous breathing pattern. The method 100 includes receiving a CVP signal, an airway pressure signal, an air flow signal, and an ECG signal of a patient from a corresponding sensor 24, 26, 28, 30 (102). The received signals for each breath of the patient are segmented (104). A surrogate signal for a respiratory muscle pressure generated by the patient is calculated for each segmented breath (106). Data indicative of cardiac activity of the patient is filtered from the surrogate muscle pressure signal (108). Peaks in the filtered signal are extracted (110). Regions of positive monotonicity, negative monotonicity, and constant values are defined on the filtered signal (112). Default assumptions of the shape of the underlying muscle pressure profile in CO and PO algorithms are modified (114). A more accurate estimate of the patient's respiratory muscle effort and the respiratory system's parameters is provided (116).

Figure 17:
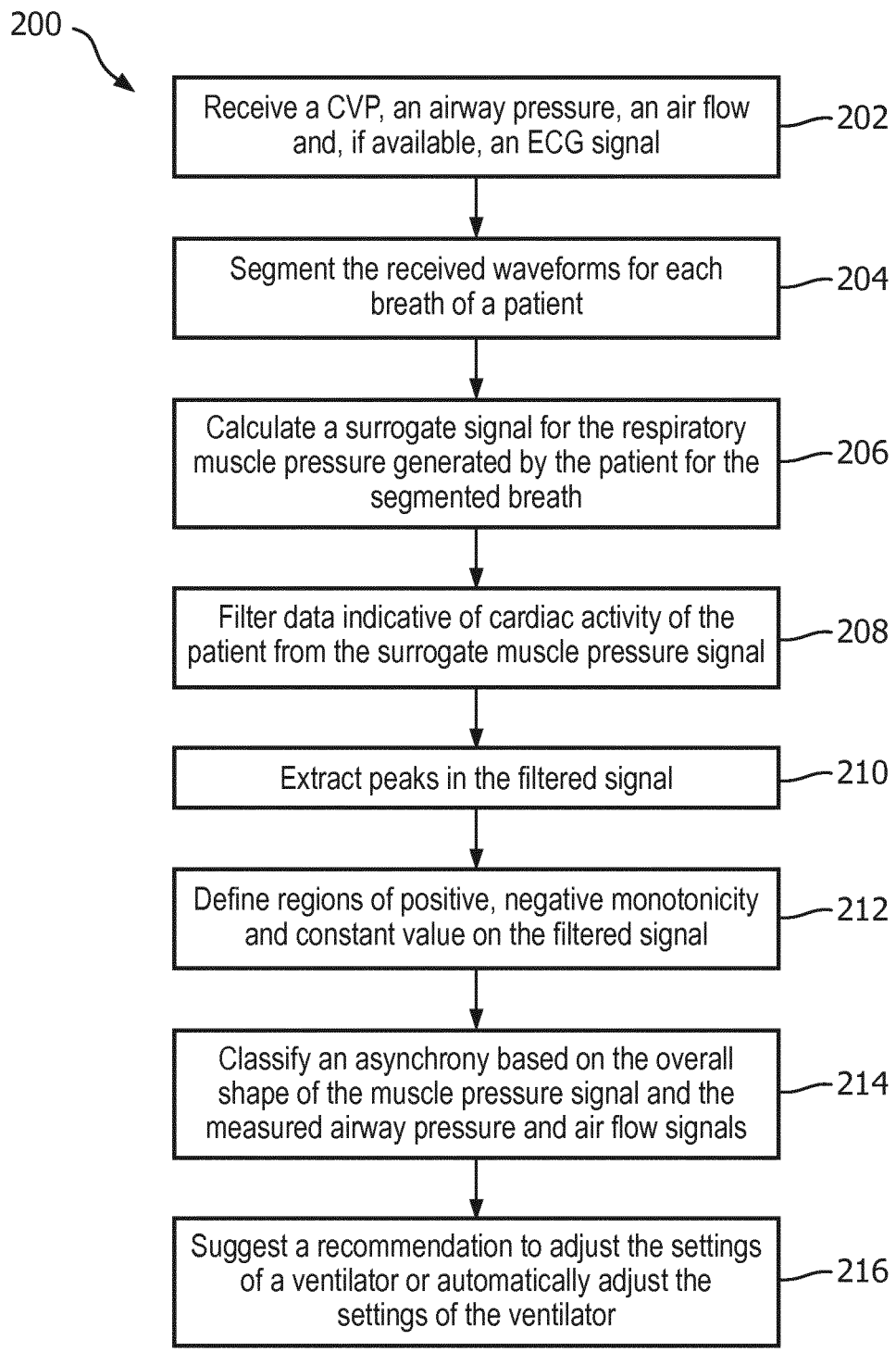
FIG. 17 shows a flow chart of an exemplary method of use for the ventilator apparatus of FIG. 14.

FIG. 17 shows a method 200 of suggesting or automatically performing a corrective action in regards to the selected ventilator settings upon detecting a patient-ventilator asynchrony event. The method 200 includes receiving a CVP signal, an airway pressure signal, an air flow signal, and an ECG signal of a patient from a corresponding sensor 24, 26, 28, 30 (202). The received signals are segmented for each breath of the patient (204). A surrogate signal for a respiratory muscle pressure generated by the patient is calculated for each segmented breath (206). Data indicative of cardiac activity of the patient is filtered from the surrogate muscle pressure signal (208). Peaks in the filtered signal are extracted (210). Regions of positive monotonicity, negative monotonicity, and constant values are defined on the filtered signal (212). An asynchrony is classified based on the overall shape of the muscle pressure signal and the measured airway pressure signal and the air flow signal (214). A recommendation to adjust the settings of a ventilator is suggested, or the settings of the ventilator are automatically adjusted (216).

The various data processing components 36, 38, 40, 42, 44, 58 and controller 60 are suitably implemented as a microprocessor programmed by firmware or software to perform the disclosed operations. In some embodiments, the microprocessor is integral to the mechanical ventilator 12, so that the data processing is directly performed by the ventilator 12. In other embodiments the microprocessor is separate from the mechanical ventilator 12, for example being the microprocessor of a desktop computer. The various data processing components 36, 38, 40, 42, 44, 58 and controller 60 of the mechanical ventilator apparatus may also be implemented as a non-transitory storage medium storing instructions readable and executable by a microprocessor (e.g. as described above) to implement the disclosed operations. The non-transitory storage medium may, for example, comprise a read-only memory (ROM), programmable read-only memory (PROM), flash memory, or other repository of firmware for the ventilator 12. Additionally or alternatively, the non-transitory storage medium may comprise a computer hard drive (suitable for computer-implemented embodiments), an optical disk (e.g. for installation on such a computer), a network server data storage (e.g. RAID array) from which the ventilator 12 or a computer can download the apparatus software or firmware via the Internet or another electronic data network, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A respiratory monitoring apparatus comprising:
a central venous pressure (CVP) sensor configured to measure a central venous pressure signal of a patient when disposed adjacent to a heart of the patient;
at least one airway sensor configured to measure airway air flow as a function of time for the patient on a mechanical ventilator; and
at least one processor programmed to process the CVP signal to generate respiratory information for the patient by operations including:
segmenting the CVP signal based on detected breath intervals;
calculating a surrogate respiratory muscle pressure signal from the segmented CVP signal and airway air flow as a function of time; and
filtering the surrogate respiratory muscle pressure signal to remove a cardiac activity component of the surrogate respiratory muscle pressure signal.

2. The apparatus of claim 1, wherein the generated respiratory information includes at least one of:
a surrogate intrapleural pressure signal determined from the segmented and filtered CVP signal, a surrogate respiratory muscle pressure waveform determined for each breath interval from the segmented and filtered CVP signal and a measured air flow signal integrated to determine an air volume signal.

3. The apparatus of claim 1, further including:
an electrocardiogram (ECG) sensor configured to measure an ECG signal;
wherein the at least one processor is programmed to perform the filtering using the ECG signal received from the ECG sensor.

4. The apparatus of claim 1, further comprising:
a mechanical ventilator configured to deliver mechanical ventilation to the patient;
wherein the at least one processor is further programmed to:
receive a start of inhalation mark as a function of time for each breath of the patient from the mechanical ventilator; and
determine breath intervals of the patient from the start of inhalation marks.

5. The apparatus of claim 1, wherein the at least one processor is programmed to:
calculate the surrogate respiratory muscle pressure as a function of time from the equation:

$$P_{mus,surr}(t)=\text{CVP}(t)-E_{cw}V_{air}(t)+P_0;$$

where $P_{mus,surr}(t)$ denotes surrogate respiratory muscle pressure, CVP(t) denotes the CVP signal, $E_{cw}$ denotes a chest wall elastance, $V_{air}(t)$ denotes a lung air volume computed as an integral of the air flow as a function of time, and $P_0$ denotes a constant.

6. The apparatus of claim 1, wherein the at least one processor is further programmed to:
detect a plurality of peaks in the segmented and filtered surrogate muscle pressure signal; and
generate the respiratory information including a respiratory muscle pressure waveform comprising respiratory muscle pressure waveform segments over time intervals delineated by the peaks.

7. The apparatus of claim 6, wherein the at least one processor is further programmed to:
   update settings of a constrained optimization algorithm and/or a parametric optimization algorithm of the mechanical ventilator based on the peak-detected muscle pressure signal.

8. A mechanical ventilation apparatus, comprising:
   a mechanical ventilator;
   at least one airway sensor configured to measure airway pressure and air flow as functions of time for the patient on the mechanical ventilator;
   at least one processor programmed to:
      receive a central venous pressure signal from a central venous pressure sensor;
      receive the air flow signal as a function of time for the patient from the at least one airway sensor;
      calculate a respiratory muscle pressure signal as a function of time for each breath of the patient from the central venous pressure signal as a function of time and the air flow signal as a function of time;
      extract at least one respiratory characteristic from the respiratory muscle pressure signal by operations including:
         filtering data indicative of cardiac activity of the patient from the respiratory muscle pressure signal;
         determining a shape of the respiratory muscle pressure signal; and
         updating settings of a constrained optimization algorithm and/or a parametric optimization algorithm of the mechanical ventilator based on the shape-detected signal.

9. The apparatus of claim 8, further including:
   an electrocardiogram (ECG) sensor configured to measure data indicative of cardiac activity of the patient;
   wherein the at least one processor is further programmed to filter data indicative of cardiac activity of the patient from the respiratory muscle pressure signal using the cardiac data received from the ECG sensor.

10. The apparatus of claim 8, wherein the at least one processor is programmed to:
    receive a start of inhalation mark as a function of time for each breath of the patient and a start of exhalation mark as a function of time for each breath of the patient from the mechanical ventilator; and
    determine a duration of each breath of the patient as a function of time from the start of inhalation and the start of exhalation marks by segmenting the received marks and the air flow signal as a function of time to determine each breath of the patient.

11. The apparatus of claim 8, wherein the at least one processor is programmed to:
    calculate the respiratory muscle pressure signal as a function of time from the received central venous pressure and air volume signals by operations including computing a difference between the central venous pressure signal and a function of the air volume signal.

12. The apparatus of claim 8, wherein the at least one processor is programmed to:
    calculate the respiratory muscle pressure signal as a function of time from the equation:

$$P_{mus,surr}(t)=\text{CVP}(t)-E_{cw}V_{air}(t)+P_0;$$

wherein $P_{mus,surr}(t)$ is the respiratory muscle pressure signal, CVP corresponds to central venous pressure, $E_{cw}$ corresponds to elastance of a chest wall, $V_{air}(t)$ denotes a lung air volume computed as an integral of the air flow as a function of time, and $P_0$ corresponds to a constant;
    display, on a display, the calculated of respiratory muscle pressure signal.

13. The apparatus of claim 8, wherein the at least one processor is programmed to:
    extract a plurality of peaks in the filtered surrogate muscle pressure signal, the peaks corresponding to a shape of the filtered signal.

14. The apparatus of claim 8, further including:
    a classification processor programmed to classify an asynchrony of the extracted signal according to at least one of:
       no asynchrony;
       ineffective triggering;
       auto-triggering;
       delayed cycling off;
       early cycling off; and
       double triggering.

15. The apparatus of claim 14, wherein the at least one processor is programmed to at least one of:
    suggest a recommendation for a medical professional to adjust the settings of the mechanical ventilator to correct the asynchrony, wherein the recommendation is displayed on the display; and
    automatically adjust the settings of the mechanical ventilator to correct the asynchrony.

16. A non-transitory storage medium storing instructions readable and executable by one or more microprocessors to perform a method of monitoring breathing patterns of a patient, the method comprising:
    receiving a central venous pressure value from a central venous pressure sensor;
    receiving values of at least one of airway pressure and air flow as a function of time for the patient from at least one airway sensor;
    segmenting the received values to determine each breath of the patient;
    calculate a surrogate signal of respiratory muscle pressure as a function of time generated by the patient on the mechanical ventilator from the equation:

$$P_{mus,surr}(t)=\text{CVP}(t)-E_{cw}V_{air}(t)+P_0;$$

wherein $P_{mus,surr}(t)$ corresponds to surrogate respiratory muscle pressure, CVP corresponds to central venous pressure, $E_{cw}$ corresponds to elastance of a chest wall, $V_{air}$ denotes a lung air volume computed as an integral of the air flow as a function of time, and $P_0$ corresponds to a constant;
    filtering data indicative of cardiac activity of the patient from the surrogate muscle pressure signal using the cardiac data received from an ECG sensor;
    extracting a plurality of peaks in the filtered signal corresponding to a shape of the filtered signal; and
    updating settings of a constrained optimization algorithm and/or a parametric optimization algorithm of the mechanical ventilator based on the peak-detected signal.

17. The non-transitory storage medium of claim 16, wherein the at least one microprocessor is further programmed to:
    receive a start of inhalation mark as a function of time for each breath of the patient and a start of exhalation mark as a function of time for each breath of the patient from the mechanical ventilator; and determine a duration of each breath of the patient as a function of time from the start of inhalation and the start of exhalation marks.

18. The non-transitory storage medium of claim 16, wherein the at least one microprocessor is further programmed to:
display, on a display, the calculated value of respiratory muscle pressure.

19. The non-transitory storage medium of claim 16, wherein the at least one microprocessor is further programmed to:
classify an asynchrony of the extracted signal according to at least one of:
no asynchrony;
ineffective triggering;
auto-triggering;
delayed cycling off;
early cycling off; and
double triggering;
and
at least one of:
suggest a recommendation for a medical professional to adjust the settings of the mechanical ventilator to correct the asynchrony, wherein the recommendation is displayed on the display; and
automatically adjust the settings of the mechanical ventilator to correct the asynchrony.

* * * * *